United States Patent
Iannotti et al.

(10) Patent No.: US 9,877,735 B2
(45) Date of Patent: Jan. 30, 2018

(54) SYSTEM AND METHOD FOR ASSISTING WITH ATTACHMENT OF A STOCK IMPLANT TO A PATIENT TISSUE

(75) Inventors: Joseph P. Iannotti, Strongsville, OH (US); Wael K. Barsoum, Bay Village, OH (US); Jason A. Bryan, Avon Lake, OH (US)

(73) Assignee: THE CLEVELAND CLINIC FOUNDATION, Cleveland ( * ) Notice: Subject to any disclaimer, the term of this patent is extended or adjusted under 35 U.S.C. 154(b) by 968 days.

(21) Appl. No.: 13/282,495

(22) Filed: Oct. 27, 2011

(65) Prior Publication Data
US 2012/0109137 A1    May 3, 2012

Related U.S. Application Data

(60) Provisional application No. 61/408,324, filed on Oct. 29, 2010.

(51) Int. Cl.
*A61B 17/56* (2006.01)
*A61B 17/17* (2006.01)
(Continued)

(52) U.S. Cl.
CPC ...... *A61B 17/1728* (2013.01); *A61B 17/1746* (2013.01); *A61B 17/1778* (2016.11);
(Continued)

(58) Field of Classification Search
CPC ............ A61B 17/1746; A61B 17/1739; A61B 2017/1778; A61B 2017/90;
(Continued)

(56) References Cited

U.S. PATENT DOCUMENTS 4,528,980 A * 7/1985 Kenna .............................. 606/80
4,841,975 A    6/1989 Woolson
(Continued)

FOREIGN PATENT DOCUMENTS

AU    2004293091 A1    6/2005
AU    2004293104 A1    6/2005
(Continued)

OTHER PUBLICATIONS

Hananouchi et al., "Tailor-Made Surgical Guide Reduces Incidence of Outliers of Cup Placement", *Clin Orthop Relat Res*, 468:1088-1095 (2010).
(Continued)

*Primary Examiner* — Tatiana Nobrega
*Assistant Examiner* — Marcela I Shirsat
(74) *Attorney, Agent, or Firm* — Norton Rose Fulbright

(57) ABSTRACT

A guide for assisting with attachment of a stock prosthetic implant to a patient tissue includes a lower guide surface configured to contact an upper implant surface of the stock prosthetic implant when a lower implant surface of the stock prosthetic implant contacts the patient tissue. An upper guide surface is accessible to a user when the lower guide surface is in contact with the upper implant surface. At least one guiding aperture extends through the guide body between the upper and lower guide surfaces at a predetermined aperture location with respect to the guide body and defines a predetermined target trajectory through the guide body. At least one of the target trajectory and the aperture location of each guiding aperture is preselected responsive to preoperative imaging of the patient tissue. A method of assisting with attachment of a stock prosthetic implant to a patient tissue is also provided.

17 Claims, 15 Drawing Sheets

(51) Int. Cl.
*A61B 17/80* (2006.01)
*A61B 17/88* (2006.01)
*A61B 17/00* (2006.01)
*A61B 17/90* (2006.01)
*A61F 2/34* (2006.01)
*A61F 2/46* (2006.01)
*A61B 34/10* (2016.01)

(52) U.S. Cl.
CPC ...... *A61B 17/8061* (2013.01); *A61B 17/1753* (2013.01); *A61B 17/8897* (2013.01); *A61B 34/10* (2016.02); *A61B 2017/00526* (2013.01); *A61B 2017/568* (2013.01); *A61B 2017/90* (2013.01); *A61F 2/34* (2013.01); *A61F 2/4609* (2013.01); *A61F 2002/3401* (2013.01); *A61F 2002/3403* (2013.01); *A61F 2002/3408* (2013.01)

(58) Field of Classification Search
CPC ........... A61B 2017/568; A61B 17/1753; A61F 2/4609; A61F 2/34; A61F 2002/3403; A61F 2002/3401
USPC ................. 606/87, 96, 97, 98, 86 R, 80, 99; 623/22.35–22.37, 22.21, 22.32
See application file for complete search history.

(56) References Cited

U.S. PATENT DOCUMENTS

| | | | |
|---|---|---|---|
| 5,098,383 A | 3/1992 | Hemmy et al. | |
| 5,217,499 A * | 6/1993 | Shelley | A61B 17/1666 606/86 R |
| 5,226,917 A | 7/1993 | Schryver | |
| 5,490,854 A | 2/1996 | Fisher et al. | |
| 5,768,134 A | 6/1998 | Swaelens et al. | |
| 5,769,856 A | 6/1998 | Dong et al. | |
| 5,871,018 A | 2/1999 | Delp et al. | |
| 5,916,219 A | 6/1999 | Matsuno et al. | |
| 5,976,148 A | 11/1999 | Charpenet et al. | |
| 6,699,289 B2 | 3/2004 | Iannotti et al. | |
| 6,855,150 B1 | 2/2005 | Linehan | |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 8,894,694 B2 * | 11/2014 | Brandon | A61B 17/1615 606/286 |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0021148 A1 | 1/2005 | Gibbs | |
| 2005/0148843 A1 | 7/2005 | Roose | |
| 2005/0203536 A1 | 9/2005 | Laffargue et al. | |
| 2005/0234461 A1 | 10/2005 | Burdulis et al. | |
| 2005/0267584 A1 | 12/2005 | Burdulis et al. | |
| 2006/0058886 A1 | 3/2006 | Wozencroft | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2007/0288030 A1 | 12/2007 | Metzger et al. | |
| 2008/0109085 A1 | 5/2008 | Tulkis et al. | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0269906 A1 | 10/2008 | Iannotti et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0012526 A1 * | 1/2009 | Fletcher | 606/96 |
| 2009/0018546 A1 | 1/2009 | Daley | |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |

(56) References Cited

U.S. PATENT DOCUMENTS

| | | |
|---|---|---|
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0157086 A1 | 6/2009 | Digeser et al. |
| 2009/0177208 A1 | 7/2009 | Strnad et al. |
| 2009/0222014 A1 | 9/2009 | Bojarksi et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274253 A1* | 10/2010 | Ure .................................. 606/91 |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1* | 7/2011 | Meridew et al. ............... 606/80 |
| 2011/0190775 A1 | 8/2011 | Ure |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |

(56) References Cited

U.S. PATENT DOCUMENTS

| | | |
|---|---|---|
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0096564 A1* | 4/2013 | Winslow et al. ............ 606/96 |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1 639 949 A1 | 3/2006 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |

(56) References Cited

FOREIGN PATENT DOCUMENTS

| | | |
|---|---|---|
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| FR | 2650174 | 2/1991 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2008188400 A | 8/2008 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | WO-2008/100541 A1 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

U.S. Barsoum U.S. Appl. No. 13/178,324, filed Jul. 7, 2011, entitled "Method and Apparatus for Providing a Relative Location Indication During a Surgical Procedure".

U.S. Iannotti et al., U.S. Appl. No. 61/408,359, filed Oct. 29, 2010, entitled "System and Method for Association of a Guiding Aid with a Patient".

U.S. Iannotti et al., U.S. Appl. No. 61/408,376, filed Oct. 29, 2010, entitled "System and Method for Assisting with Arrangement of a Stock Instrument with Respect to a Patient Tissue".

U.S. Iannotti et al., U.S. Appl. No. 61/408,392, filed Oct. 29, 2010, entitled "System of Preoperative Planning and Provision of Patient-Specific Surgical Aids".

European Examination Report, Application No. EP11782293.2, Apr. 14, 2016.

Taylor et al, "Computer-Integrated Surgery, Technology and Clinical Applications", The MIT Press, Cambridge, MA, London, UK, pp. 451-463.

Hofmann et al, "Natural-Knee II System", Intermedics Orthopedics, Austin, TX, 1995.

\* cited by examiner

SYSTEM AND METHOD FOR ASSISTING WITH ATTACHMENT OF A STOCK IMPLANT TO A PATIENT TISSUE

RELATED APPLICATION

This application claims priority from U.S. Provisional Application No. 61/408,324, filed Oct. 29, 2010, the subject matter of which is incorporated herein by reference in its entirety.

TECHNICAL FIELD

The present invention relates to a system and method for use of a surgical guide and, more particularly, to a system and method for use of a surgical guide for assisting with attachment of a stock implant to a patient tissue.

BACKGROUND OF THE INVENTION

The efficient functioning of the hip joints is important to the well-being and mobility of the human body. Each hip joint includes the upper portion of the femur, which terminates in an offset bony neck surmounted by a ball-headed portion known as the femoral head. The femoral head rotates within a socket, known as the acetabulum, in the pelvis to complete the hip joint. Diseases such as rheumatoid- and osteo-arthritis can cause erosion of the cartilage lining of the acetabulum so that the ball of the femur and the hip bone rub together, causing pain and further erosion. Bone erosion may cause the bones themselves to attempt to compensate for the erosion which may result in the bone becoming deformed. This misshapen joint may cause pain and may eventually cease to function altogether.

Operations to replace the hip joint with an artificial implant are well-known and widely practiced. Generally, the hip prosthesis will be formed of two components, namely: an acetabular, or socket, component which lines the acetabulum, and a femoral, or stem, component which includes a weight-bearing ball and replaces the femoral head. During the surgical procedure for implanting the hip prosthesis, the remaining cartilage or damaged tissue is removed from the acetabulum using a reamer such that the native acetabulum will accommodate the outer surface of the acetabular component of the hip prosthesis. The acetabular cup component of the prosthesis can then be inserted into the prepared acetabulum. In some arrangements, the acetabular cup component may simply be held in place by a tight fit with the bone. However, in other arrangements, additional fixing means such as screws and/or bone cement may be used. The use of additional fixing means helps to provide stability in the early stages after the prosthesis has been inserted. In some modern prosthesis, the acetabular cup component may be coated on its external surface with a bone growth promoting substance which will encourage bone ingrowth which helps to hold the acetabular component in place. The bone femoral head also is removed during the surgical procedure, and the femur shaft hollowed out using reamers and rasps to accept the femoral component of the prosthesis. The stem portion of the prosthesis is inserted into the femur and secured therein to complete the hip joint replacement.

In order to strive toward desired performance of the combined acetabular and femoral hip prosthesis components, the acetabular cup portion must be properly positioned in the acetabulum. This is particularly important since incorrect positioning of the acetabular cup component can lead to the prosthetic hip joint suffering from dislocations, a decreased range of motion, and possibly eventual loosening and/or failure of one or both components of the joint.

It is generally believed that there is a preferred orientation for the acetabular cup prosthesis component to provide a full range of motion and to minimize the risk of dislocation. Some example orientations of the acetabular cup prosthesis relative to the acetabular face are 45° to 50° from the vertical and rotated forward to 15° to 20° of anteversion. This broadly replicates the natural angle of the acetabulum. However, the specific angular orientation of the acetabular cup portion varies from patient to patient.

In hip replacement surgery, the acetabular cup portion of the prosthesis is usually oriented in the acetabulum by using an acetabulum positioning instrument. One example of such a positioner is a horizontal arm that is aligned parallel to a predetermined native tissue of the patient when the acetabular cup portion is oriented at a preferred abduction angle. This positioner is therefore sensitive to the position of the patient on the operating table for accuracy. The acetabular cup placement is typically done using an acetabular cup positioner and visual adjustment of the acetabular cup portion to ensure that the horizontal arm of the positioner is approximately parallel to the selected reference tissue (or axis) of the patient. The user of the positioner may also view the position of the acetabular cup portion relative to a second arm on the acetabular cup positioner which is positioned at a preset angle, to assist with positioning the acetabular cup at the correct abduction angle.

However, despite this known positioning procedure, the orientation of the acetabular cup portion in the replaced hip can deviate from the desired orientation. This may be due to one or more factors. First, the positioning of the acetabular cup is usually judged by eye. As the position to be judged by the user is a compound angle, it may be particularly difficult to visualize. Second, since the natural face of the acetabulum is not uniform and—where the hip is arthritic—may be distorted by osteophytes, the acetabulum is not generally a reliable guide for orientating the acetabular cup portion of the prosthetic joint. A third problem is that the prior art mechanical alignment guides usually rely on the pelvis being in a set position which may itself be difficult to judge, particularly in an obese patient. In view of these difficulties, the acetabular cup portion may sometimes be actually located via surgery as much as 20° from the desired/planned position.

The above factors and issues encountered in surgical hip intervention have analogues in the shoulder surgery arena. For example, generally the normal glenoid retroversion of a given patient may fall within a range of approximately 20° (5° of anteversion and 15° of retroversion). (The version of the glenoid is defined as the angle between the plane of the glenoid fossa and the plane of the scapula body.) In the pathologic state, glenoid bone loss may result in a much larger range of version angles.

One goal of shoulder surgery may be to modify the pathologic bone to correct pathologic version to be within the normal range or the normal version of the patient's native anatomy before the bone loss occurred. During surgery, and particularly minimally invasive procedures, the plane of the scapula may be difficult or impossible to determine by direct visual inspection, resulting in the need for assistive devices or methods to define both the pathologic version present at the time of surgery and the intended correction angle.

It is generally believed that there is a preferred orientation for the glenoid component to provide a full range of motion and to minimize the risk of dislocation. Some example orientations of the glenoid prosthesis relative to the glenoid face are about 5° of anteversion to about 15° of retroversion; average version is about 1-2° of retroversion. This broadly replicates the natural angle of the glenoid. However, the specific angular orientation of the glenoid portion varies from patient to patient.

With a view to overcoming these disadvantages, some arrangements have been recently suggested in which a three-dimensional intraoperative computer imaging surgical navigation system is used to render a model of the patient's bone structure. This model is displayed on a computer screen and the user is provided with intraoperative three-dimensional information as to the desired positioning of the instruments and the glenoid component of the prosthetic implant. However, surgical navigation arrangements of this type are not wholly satisfactory since they generally use only a low number of measured landmark points to register the patient's anatomy and to specify the angle of the prosthetic implant component (e.g., a glenoid component), which may not provide the desired level of accuracy. Further, the information provided by such systems may be difficult to interpret and may even provide the user with a false sense of security. Moreover, these systems are generally expensive to install and operate and also have high user training costs. Various proposals for trial prosthetic joint components have been made in an attempt to overcome the problems associated with accurately locating the acetabular cup portion of the prosthetic implant. While these trial systems may help with checking whether the selected position is correct, they are not well-suited to specify the correct position initially, and thus there still is user desire for a system which may assist a user in placement of prosthetic implant component in a prepared native tissue site.

SUMMARY OF THE INVENTION

In an embodiment of the present invention, a method of attaching a stock prosthetic implant to a patient tissue is described. The stock prosthetic implant includes a plurality of fastener apertures extending therethrough. A lower implant surface of the stock prosthetic implant is placed into contact with the patient tissue in a predetermined implant orientation. A guide having a lower guide surface contoured to substantially mate with at least a portion of an upper implant surface of the stock prosthetic implant, an upper guide surface spaced longitudinally apart from the lower guide surface by a guide body, and at least one guiding aperture extending through the guide body between the upper and lower guide surfaces at a predetermined aperture location with respect to the guide body is provided. A predetermined target trajectory is defined through the guide body with a chosen guiding aperture. At least one of the target trajectory and the aperture location of each guiding aperture is preselected responsive to preoperative imaging of the patient tissue. The lower guide surface is placed into mating contact with at least a portion of the upper implant surface in a predetermined relative guide/implant orientation. The chosen guiding aperture is placed into a collinear relationship with a chosen one of the fastener apertures. A surgical tool is guided through the chosen guiding aperture and the corresponding chosen fastener aperture and inserting the surgical tool into the patient tissue along the target trajectory to create a fastener cavity in the patient tissue, and/or a fastener is guided through the chosen fastener aperture and into the patient tissue along the target trajectory.

In an embodiment of the present invention, a guide for assisting with attachment of a stock prosthetic implant to a patient tissue is described. A lower guide surface is configured to contact an upper implant surface of the stock prosthetic implant when a lower implant surface of the stock prosthetic implant is in contact with the patient tissue. At least a portion of the lower guide surface is contoured to substantially mate with at least a portion of the upper implant surface. An upper guide surface is spaced longitudinally apart from the lower guide surface by a guide body. The upper guide surface is accessible to a user when the lower guide surface is in contact with the upper implant surface. At least one guiding aperture extends through the guide body between the upper and lower guide surfaces at a predetermined aperture location with respect to the guide body. The at least one guiding aperture defines a predetermined target trajectory through the guide body. The at least one guiding aperture is collinear with a corresponding at least one fastener aperture in the stock prosthetic implant when the lower guide surface is mated with the upper implant surface. At least one of the target trajectory and the aperture location of each guiding aperture is preselected responsive to preoperative imaging of the patient tissue.

In an embodiment of the present invention, a guide for assisting with attachment of a stock prosthetic implant to a patient tissue is provided. A lower guide surface is configured to contact an upper implant surface of the stock prosthetic implant when a lower implant surface of the stock prosthetic implant is in contact with the patient tissue. The lower guide surface is contoured to substantially mate with at least a portion of the upper implant surface. An upper guide surface is spaced longitudinally apart from the lower guide surface by a guide body. The upper guide surface is accessible to a user when the lower guide surface is in contact with the upper implant surface. An orienting feature is configured to enter a predetermined orienting relationship with a previously placed landmark while the lower guide surface is in mating contact with at least a portion of the upper implant surface in a predetermined relative guide/implant orientation.

BRIEF DESCRIPTION OF THE DRAWINGS

For a better understanding of the invention, reference may be made to the accompanying drawings, in which.

DESCRIPTION OF EMBODIMENTS

Figure 1:
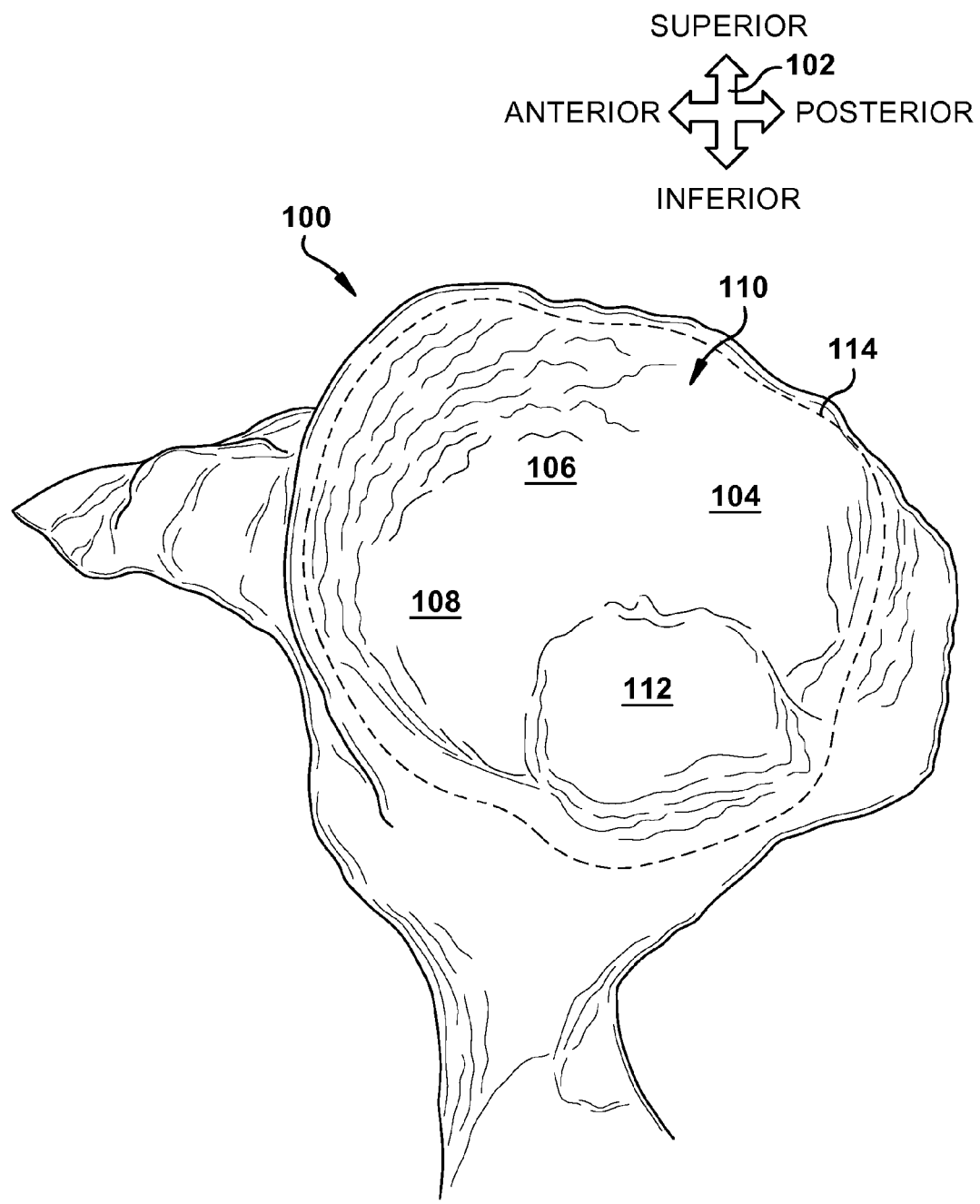
FIG. 1 is a top view of a first example use environment.

FIG. 1 depicts a portion of the external surface of a (left) hip bone 100, which is an example of a possible patient tissue use environment for the described systems, apparatuses, and methods. Directional arrow 102 indicates the superior/inferior and anterior/posterior directions. The body of ischium, body of ilium, and body of pubis are shown generally at 104, 106, and 108, respectively. The acetabulum 110, which is formed in part by these three bodies 104, 106, and 108, has a recessed acetabular fossa 112 and is surrounded by an acetabular margin 114 (shown approximately in FIG. 1 via dashed line).

The patient tissue is shown and described herein at least as a hip bone and the implant component is shown and described herein at least as an acetabular prosthetic hip component, but the patient tissue and corresponding implant component could be any desired types such as, but not limited to, hip joints, shoulder joints, knee joints, ankle joints, phalangeal joints, metatarsal joints, spinal structures, long bones (e.g., fracture sites), or any other suitable patient tissue use environment for the present invention. For example, the implant component could be an internal fixation device (e.g., a bone plate), a structure of a replacement/prosthetic joint, or any other suitable artificial device to replace or augment a missing or impaired part of the body. The implant component will be described herein as a prosthetic implant component.

The term "lateral" is used herein to refer to a direction indicated by directional arrow 102 in FIG. 1; the lateral direction in FIG. 1 lies substantially within the plane of the drawing and includes all of the superior, inferior, anterior, and posterior directions. The term "longitudinal" is used herein to refer to a direction defined perpendicular to the plane created by directional arrow 102, with the longitudinal direction being substantially into and out of the plane of the drawing in FIG. 1 and representing the proximal (toward the medial line of the body) and distal (out from the body) directions, respectively.

Figure 2:
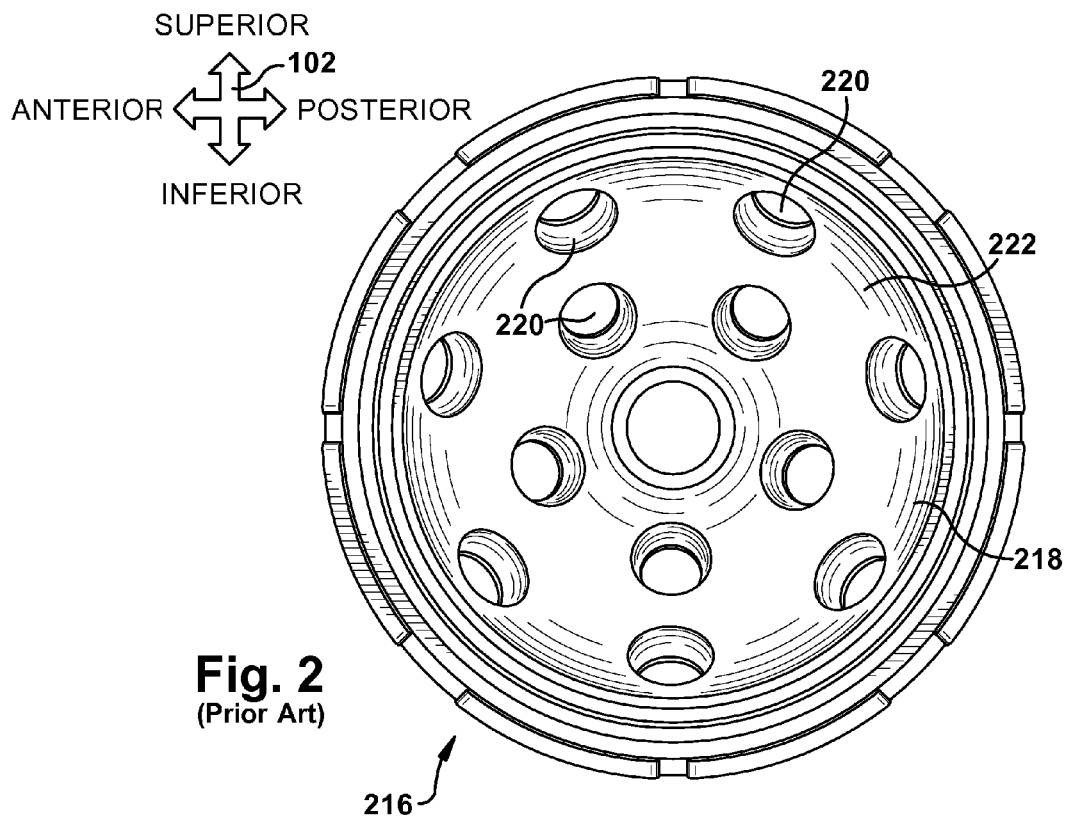
FIG. 2 is a top view of a first prior art prosthetic component.
Figure 3:
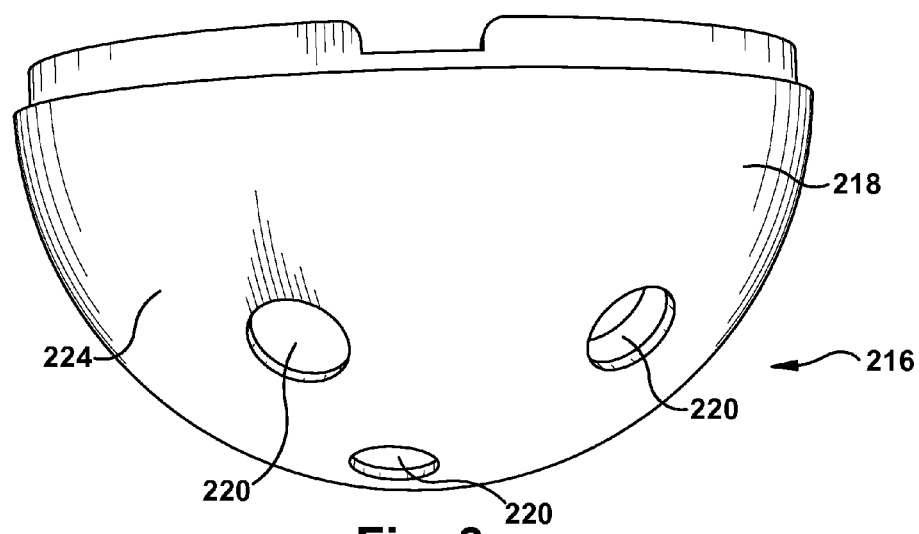
FIG. 3 is a side view of the prior art prosthetic component of FIG. 2.

FIGS. 2 and 3 are side and top views, respectively, of a prior art stock prosthetic implant, and, more specifically, of a stock acetabular cup implant 216 of a stock hip prosthesis.

The term "stock" is used herein to indicate that the prosthetic component indicated is not custom-manufactured or -configured for the patient, but is instead provided as a standard inventory item by the prosthetic manufacturer. A particular stock component may be selected by the user from a product line range of available components, with the user specifying a desired configuration, general size (e.g., small, medium, large), material, or any other characteristic of the component. Indeed, the stock component may be manufactured only after the user has selected the desired options from the range of choices available. However, the stock component is differentiated from a custom-manufactured or bespoke component in that the stock component is agnostic and indifferent regarding a particular patient anatomy during the design and manufacturing processes for a prosthetic implant intended for that patient, while the patient anatomy is an input into at least one design and/or manufacturing process for a custom-manufactured component. The following description presumes the use of a stock prosthetic component, though one of ordinary skill in the art will be able to provide for the use of the present invention with a custom-manufactured component, instead.

The acetabular cup implant 216 comprises a parti-spherical acetabular shell 218 and a plurality of prosthetic apertures, described herein as fastener apertures 220, extending through the thickness of the acetabular shell between an upper implant surface 222 and a lower implant surface 224. The below description of "fastener apertures" 220 does not presume that each of such are configured and/or intended to actually receive a fastener, but is done solely for ease of description herein. The acetabular cup implant 216 is generally made from metal or another durable, biocompatible material and is fastened securely into an acetabulum 110 during a hip replacement procedure. An acetabular liner (not shown), generally made of a polymer or another material having desirable lubricity and durability properties, is then attached within the acetabular shell 218 and the acetabular liner cradles the femoral ball component (not shown) in the finished prosthetic hip joint. The fastener apertures 220 are configured to accept fasteners (not shown), and the acetabular shell 218 usually includes more fastener cavities than the number of fasteners expected to be used, to provide flexibility for the user in selecting fastener placement for a particular patient. The multiplicity of fastener apertures 220, beyond the number intended to receive fasteners, also may provide advantages in weight savings and increased flexibility of the acetabular cup implant 216.

Much of the success of a prosthetic joint replacement arises from secure affixation of the acetabular cup implant 216 to the hip bone 100, and anchoring of the fasteners into robust bony matter contributes to a suitably snug fit between the acetabular cup implant and the hip bone. However, pathological anatomy of the hip bone 100 may affect where the fasteners can be securely placed. The native and pathological anatomies differ from patient to patient, so preoperative patient imaging scans may be used to preoperatively plan desired locations and trajectories for the fasteners to be inserted through the emplaced acetabular cup implant 216 into the hip bone 100. However, and particularly during minimally invasive surgeries, very little of the hip bone 100 is visible to the user, and the visible portion of the hip bone may be located at the distal end of a "tunnel" of surrounding soft tissue temporarily cleared out of the way by the user; accordingly, available maneuvering space at the surgical site may be severely restricted. In addition, the patient's hip joint may be actually canted slightly differently during the surgical procedure than planned preoperatively. These are among the factors which may result in a preoperative location/trajectory plan for a particular fastener being very difficult and time-consuming for a user to actually perform in an operative environment.

To aid with carrying out a preoperative plan for attaching a stock prosthetic implant to a patient tissue, a guide 426 may be provided, according to a first embodiment of the present invention. The guide 426, shown in various optional configurations in FIGS. 4-10, is at least partially custom-manufactured for a particular patient responsive to preoperative imaging of the patient tissue. For example, the guide 426 may be wholly custom-made (e.g., using rapid prototyping techniques) or may be modified from a stock guide or guide blank (not shown). It is contemplated that at least a part of the guide 426 is a patient-specific, single-use, bespoke feature suited only for use at the indicated surgical site, though one of ordinary skill in the art could create a guide (not shown) which uses a patient-specific "disposable" structure connected to a stock, generic "reusable" carrier.

Regardless of the whole/partial custom manufacture status, the guide 426 may be configured responsive to at least one of preoperative imaging of the patient tissue and preoperative selection of the stock prosthetic implant. The location and target trajectory of each fastener of the implant are predetermined by a user before the guide 426 is associated with the patient tissue. This predetermination may occur intraoperatively, as the user is able to directly see the condition of the surgical site. However, it is contemplated that a predetermination of the desired insertion location and target trajectory of each fastener could be accomplished preoperatively, with reference to preoperative imaging of the patient tissue. For example, a system similar to that of co-pending U.S. patent application Ser. No. 13/282,550, filed Oct. 27, 2011, titled "System of Preoperative Planning and Provision of Patient-Specific Surgical Aids" and claiming priority to U.S. Provisional Patent Application No. 61/408,392, filed Oct. 29, 2010 and titled "System of Preoperative Planning and Provision of Patient-Specific Surgical Aids", the entire contents of both of which are incorporated herein by reference, or any suitable preoperative planning system, could be used. In this manner, a user can create a patient tissue model for observation, manipulation, rehearsal, or any other pre-operative tasks.

The term "model" is used herein to indicate a replica or copy of a physical item, at any relative scale and represented in any medium, physical or virtual. The patient tissue model may be a total or partial model of a subject patient tissue, and may be created in any suitable manner. For example, and as presumed in the below description, the patient tissue model may be based upon computer tomography ("CT") data imported into a computer aided drafting ("CAD") system. Additionally or alternatively, the patient tissue model may be based upon digital or analog radiography, magnetic resonance imaging, or any other suitable imaging means. The patient tissue model will generally be displayed for the user to review and manipulate preoperatively, such as through the use of a computer or other graphical workstation interface.

During preoperative planning, the user can view the patient tissue model and, based upon knowledge of other patient characteristics (such as, but not limited to, height, weight, age, and activity level), then choose a desired stock prosthetic implant. Because three-dimensional image models are available of many stock prosthetic implants, the user may be able to "install" the stock prosthetic implant virtually in the patient tissue model via a preoperative computer simulation. During such a simulation, the user can adjust the position of the stock prosthetic implant with respect to the patient tissue, even to the extent of simulating the dynamic interaction between the two, to refine the selection, placement, and orientation of the stock prosthetic implant for a desired patient outcome.

Once a chosen stock prosthetic implant has been virtually placed in a desired position and orientation with respect to the patient tissue (it will be understood that some mechanical modification might need to be made to the native patient tissue to accomplish this implant placement), the fastener placement can also be planned through the use of the computer simulation, with consideration of the location, amount, and pathology of the patient tissue, or any other desired factors, being taken into account in fastener placement planning. By hand and/or with automatic computer assistance, the user can experiment with various fastener sizes, placements, and orientations for securing the stock prosthetic implant to the patient tissue. When the fastener positioning has been finalized, with the implant virtually positioned in a predetermined implant orientation with respect to the patient tissue, a location and target trajectory can be defined for each of the fasteners to follow during installation. The term "trajectory" is used herein to indicate an invisible line along which an elongate body will travel under guidance from the trajectory-defining structure.

The fastener location and target trajectory information for the particular patient tissue achieved via preoperative imaging and/or computer simulation/modeling may be transferred to a physical aid for the user through the custom manufacture of a guide 426, such as those shown in various configurations in FIGS. 4-10. When the preoperative planning has been finalized, a virtual guide 426 is generated at a predetermined guide orientation with respect to the virtual implant and the virtual patient tissue. The user may then have the opportunity to adjust the virtual guide 426, if desired, before a physical guide 426 is produced.

Figure 4:
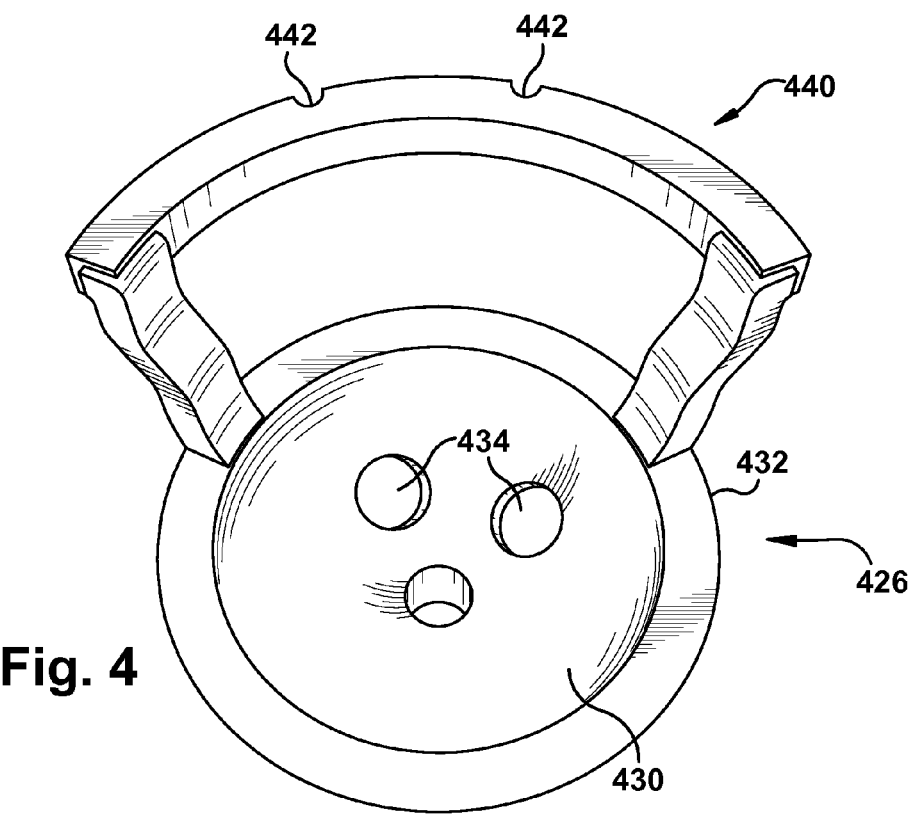
FIG. 4 is a top view of a first embodiment of the present invention in a first configuration.
Figure 5:
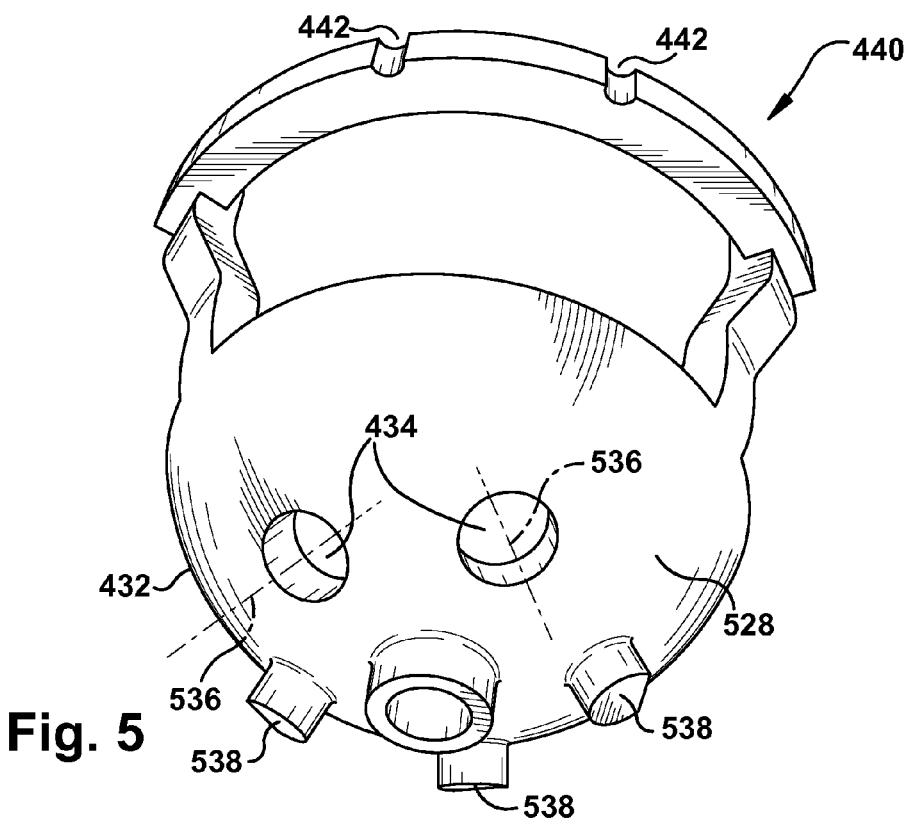
FIG. 5 is a perspective bottom view of the embodiment of FIG. 4 in the first configuration.

With reference to FIGS. 4-5, the guide 426 (hereafter described as being physical, not virtual) includes a lower guide surface 528 (visible in FIG. 5) configured to contact an upper implant surface 222 of the stock prosthetic implant, here presumed to be an acetabular cup implant 216, when the lower implant surface 224 is in contact with the acetabulum 110. At least a portion of the lower guide surface 528 is contoured to substantially mate with at least a portion of the upper implant surface 222, as will be discussed below. The term "mate" is used herein to indicate a relationship in which the contours of two structures are at least partially matched or coordinated in at least two dimensions. For example, both the lower guide surface 528 and the upper implant surface 222 could have profiles that are concavely curved, convexly curved, planar/linear, or any combination of those or other profile shapes. The guide 426 also includes an upper guide surface 430 spaced longitudinally apart from the lower guide surface 528 by a guide body 432. The upper guide surface 430 is accessible to a user when the lower guide surface 528 is in contact with the upper implant surface 222.

The patient's name, identification number, surgeon's name, and/or any other desired identifier may be molded into, printed on, attached to, or otherwise associated with the guide 426 in a legible manner. The guide 426 may be made by any suitable method such as, but not limited to, selective laser sintering ("SLS"), fused deposition modeling ("FDM"), stereolithography ("SLA"), laminated object manufacturing ("LOM"), electron beam melting ("EBM"), 3-dimensional printing ("3DP"), contour milling from a suitable material, computer numeric control ("CNC"), other rapid prototyping methods, or any other desired manufacturing process.

At least one guiding aperture 434 extends through the guide body 432 between the upper and lower guide surfaces 430 and 528 at a predetermined aperture location with respect to the guide body (i.e., a predetermined placement of the guiding aperture 434 on the guide body). As shown in FIGS. 4-5, the at least one guiding aperture 434 defines a predetermined target trajectory 536 through the guide body 432. At least one of the target trajectory 536 and the aperture location of each guiding aperture 434 can be preselected responsive to preoperative imaging of the patient tissue, as previously described. When the guide 426 is placed atop the acetabular cup implant 216 as described above (with the lower guide surface 528 substantially mated with at least a portion of the upper implant surface 222), at least one of the guiding apertures 434 is collinear with a corresponding fastener aperture 220 in the acetabular cup implant, as will be discussed below. The term "collinear" is used herein to indicate that central axes of each of two structures lie along the same line. However, the diameters of the "collinear" guiding apertures 434 and fastener apertures 220 could differ from each other. In short, the aperture locations of the guiding apertures 434 are preselected to facilitate placement of a fastener into the stock prosthetic implant (e.g., the acetabular cup implant 216 for the embodiment of FIGS. 4-10) and the underlying patient tissue at a preselected fastener location and a preselected fastener trajectory after removal of the guide 426 from the stock prosthetic implant.

The lower guide surface 528 shown in FIG. 5 includes at least one locating protrusion 538. Each of the locating protrusions 538, when present, extends from the lower guide surface 528 and is configured to nest into, or mate with, a preselected fastener aperture 220 of the acetabular cup implant 216, to assist with mating of the lower guide surface with at least a portion of the upper implant surface 222. As can be seen in FIG. 5, the locating protrusions 538 in the depicted embodiment are simple protrusions and are not configured to accept a fastener.

An orienting feature 440, such as the depicted extension in FIGS. 4-5, may be provided to the guide 426. As shown here, for use with the acetabular cup implant 216, the orienting feature 440 may extend, perhaps substantially, longitudinally and/or laterally from the guide 426, but the direction, amount, and type of extension will depend upon the location and type of body tissue with which the guide 426 is being used. The orienting feature 440 may be configured to enter a predetermined orienting relationship with a landmark (not shown), such as a guide pin, wire, marking, and/or other location indicator previously placed in a predetermined relationship with the patient tissue, such predetermined orienting relationship occurring when the lower guide surface 528 is in mating contact with at least a portion of the upper implant surface 222 in a predetermined relative guide/implant orientation. (The predetermined relative guide/implant orientation is achieved when the guide 426 and acetabular cup implant 216 are mated in a desired manner, as predetermined via preoperative imaging and/or analysis.) The landmark may be any suitable two- or three-dimensional landmark such as, but not limited to, a native or acquired anatomical feature of the patient tissue and/or a separately provided landmark placed with the assistance of a guide as disclosed in co-pending U.S. patent application Ser. No. 13/282,509, filed Oct. 27, 2011, titled "System and Method for Association of a Guiding Aid with a Patient Tissue" and claiming priority to U.S. Provisional Patent Application No. 61/408,359, filed Oct. 29, 2010 and titled "System and Method for Association of a Guiding Aid with a Patient Tissue", the entire contents of both of which are incorporated herein by reference. The landmark could also or instead be placed using a robotic surgical aid, adjustable reusable (e.g., "dial-in") tools, intraoperative imaging, or any other suitable placement aid. For example, a portion of the orienting feature 440 could be configured to mate with a preselected surface of the patient tissue acting as a landmark such that the mating of the orienting feature and the patient tissue indicates that the predetermined orienting relationship between the orienting feature and this patient tissue landmark has been achieved.

Optionally, an original landmark could have been previously placed, then removed for any reason (e.g., to facilitate machining of the acetabulum 110 surface). A second landmark may then be placed at the same location and with the same location as the original landmark, such as via reusing the cavity in the surface left by the removal of the original landmark. Indeed, the remaining cavity in the surface itself may serve a landmarking function. Through these or any other such transformations of physical manifestations, the position information represented by the original landmark and preoperatively planned may be preserved and used during various stages of the surgical procedure regardless of the way in which that position landmark is made available to the user at those various stages. Optionally, the orienting feature 440 may include an orienting indicator 442. When present, the orienting indicator 442 may be configured to achieve a predetermined signaling relationship (the signaling relationship being directly related to the orienting relationship) with the landmark, as will be described below, while the guide 426 and the stock prosthetic implant—here, the acetabular cup implant 216—are in the predetermined relative guide/implant orientation. For example, in the first configuration of the first embodiment shown in FIGS. 4-5, the orienting feature 440 is a bridge-type structure extending from the guide body 432 and the orienting indicators 442 are notches in the orienting feature 440, each shaped to somewhat closely surround at least a portion of the diameter of a guide pin or other three-dimensional landmark to achieve the predetermined signaling relationship. The landmark(s) were previously placed in any suitable manner in predetermined locations at the surgical site. Accordingly, the predetermined signaling relationship between the landmark(s) and the orienting indicator(s) 442 assists the user in placing the guide 426 into a predetermined guide orientation with respect to the patient tissue.

When the guide 426 and the stock prosthetic implant are held in a predetermined relative guide/implant orientation (e.g., through the use of locating protrusions 538, frictional engagement, any other mechanical linkage [e.g., nesting], or even merely coordinated movement of each by the user), then the stock prosthetic implant is manipulated in concert with the guide. Accordingly, movement of the guide 426 into the predetermined guide orientation—as signaled by coordination of the landmark(s) and the orienting feature 440—will concurrently move the stock prosthetic implant into a predetermined implant orientation with respect to the patient tissue. One of ordinary skill in the art can readily preoperatively plan the placement and type of landmark(s), as well as the structure and type of orienting feature(s) 440 and/or orienting indicator(s) 442 to assist the user in guiding the stock prosthetic implant into the predetermined implant orientation and/or location with respect to the patient tissue for a particular application of the present invention.

While the orienting indicator 442 is shown in FIGS. 4-5 as being a notch, any suitable structure, notch-like or otherwise, could be used as an orienting indicator. For example, the orienting indicator 442 could be a lug extending from the orienting feature 440, a visual indicator such as a line drawn or etched on the orienting protrusion, or even a mechanical system such as a latch or trip-wire.

Figure 6:
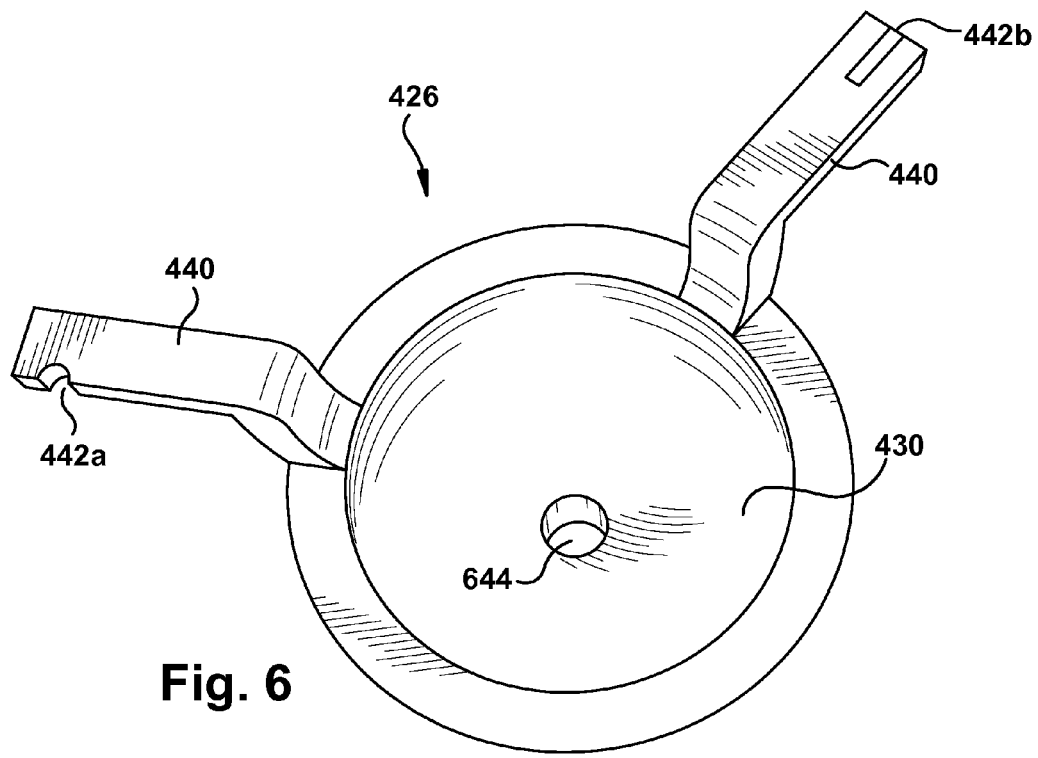
FIG. 6 is a top view of the embodiment of FIG. 4 in a second configuration.
Figure 7:
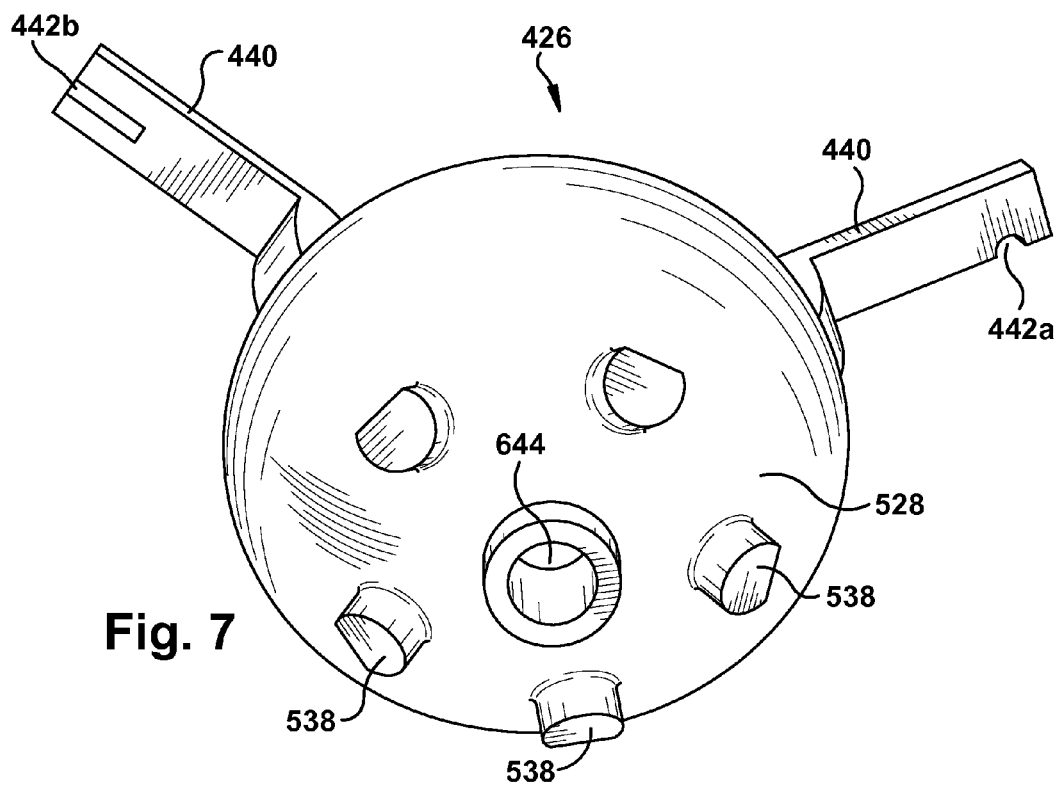
FIG. 7 is a bottom view of the embodiment of FIG. 6 in the second configuration.

As another example, a second configuration of the first embodiment of the present invention is shown in FIGS. 6-7. Structures of FIGS. 6-7 that are the same as or similar to those described with reference to FIGS. 4-5 have the same reference numbers. As with all alternate configurations shown and described herein, description of common elements and operation similar to those in previously described configurations will be omitted, for clarity. In the second configuration, the guide 426 includes multiple locating protrusions 538 and multiple orienting features 440. One of the orienting features 440 includes a notchlike orienting indicator 442a configured to interact with a landmark in an active (e.g., mechanically interacting) signaling relationship, and the other of the orienting features 440 includes a more passive orienting indicator 442b, which is depicted here as an inscribed line on the orienting feature and is configured to provide a more passive (e.g., visually observed) signaling relationship with a landmark.

As depicted in FIGS. 6-7, the guide 426 may include at least one central guide aperture 644 extending through the guide body 432 between the upper and lower guide surfaces 430 and 528. The central guide aperture 644 may be configured to accept a landmark placed in a predetermined relationship with the patient tissue. For example, the central guide aperture 644 of the second configuration is substantially centrally located in the guide body 432. If a central landmark (not shown) is placed in a similarly central location of the patient tissue at the surgical site and accepted through the central guide aperture 644, the guide body 426 could pivot about that central landmark (as if on an axis) under rotational force exerted by the user. In such manner, the guide 426 (and, by extension, the stock prosthetic implant when held in the predetermined relative guide/implant relationship) can initially be placed in a desired position with respect to the patient tissue—agnostic of rotational orientation—and then the rotational orientation can be set via pivoting of the guide and stock prosthetic implant about the central landmark until the orienting feature 440 achieves the predetermined orienting relationship with an other landmark, spaced apart from the central landmark. Optionally the central landmark could be a guidewire (not shown), such as that disclosed in co-pending U.S. patent application Ser. No. 13/178,324, titled "Method and Apparatus for Providing a Relative Location Indication During a Surgical Procedure" and filed Jul. 7, 2011, the entire contents of which are incorporated herein by reference.

As an alternative to this agnostic placement of the guide 426 and nested/attached stock prosthetic implant at the surgical site and subsequent rotation into position, the guide 426 and the stock prosthetic implant could be concurrently placed into contact with at least one landmark (which could include the central landmark) at a location spaced apart from the patient tissue at the surgical site. For example, a landmark could be an elongate guide pin, and a notch-like orienting indicator 442 could be placed into the signaling relationship with a protruding end of the guide pin some distance from the patient tissue. In this optional situation, the stock prosthetic implant would be guided into the predetermined implant orientation concurrently with being brought into contact with the patient tissue as the orienting indicator 442 slides along the length of the guide pin via a rail-like dynamic guiding technique.

Figure 8:
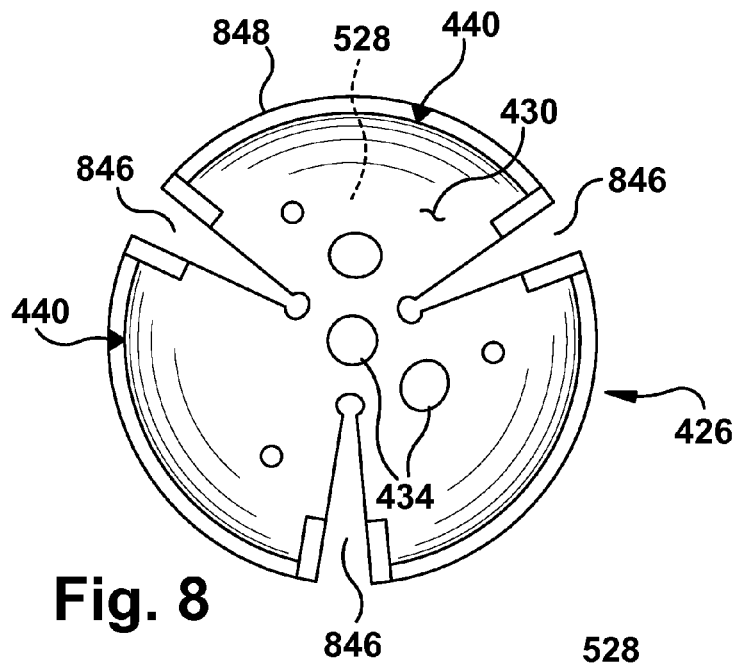
FIG. 8 is a top view of the embodiment of FIG. 4 in a third configuration.
Figure 9:
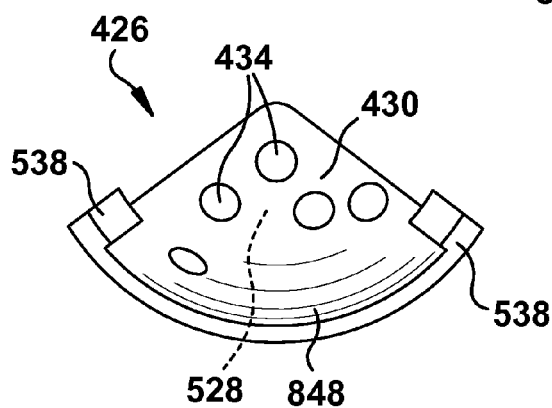
FIG. 9 is a top view of the embodiment of FIG. 4 in a fourth configuration.
Figure 10:
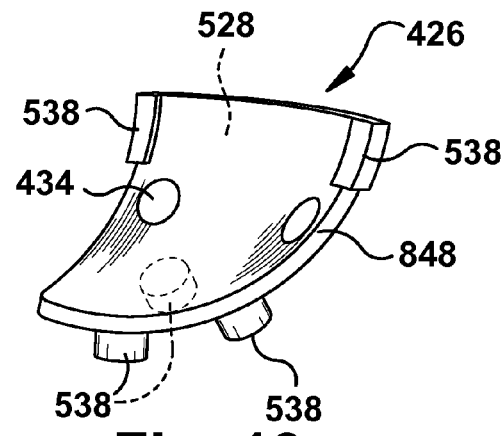
FIG. 10 is a top view of the embodiment of FIG. 4 in a fifth configuration.

FIGS. 8, 9, and 10 depict third, fourth, and fifth configurations, respectively, of the first embodiment of the present invention. In the third configuration of FIG. 8, the guide 426 is configured to substantially mate with a fairly large portion of the acetabular cup implant 216. Relief slots 846 may extend laterally inward from an outer guide rim 848 and, when present, can help provide for a temporary reduction in circumference of the guide 426 under lateral force (e.g., a squeeze by the user) to elastically deform the guide 426 and facilitate placement of the guide into the acetabular cup implant 216. When the lateral force is released, the guide 426 expands back to the original circumference to nest closely within the acetabular cup implant 216.

As shown in FIG. 8, a plurality of two-dimensional orienting features 440 are provided on the upper guide surface 430. The orienting features 440 shown in FIG. 8 are visual indications—here, darkened carets—on the outer guide rim 848 and may help guide the user in placing the guide 426 in a predetermined mating relationship with the stock prosthetic implant, to assist in carrying out the preoperative plan including the placement of the fasteners to secure the stock prosthetic implant in a desired manner. For example, the orienting features 440 shown in FIG. 8 may be placed to correspond to (e.g., line up radially with) the positions of one or more landmarks previously placed on or near the acetabulum 110. Optionally, the orienting features 440 may be placed to correspond to the position(s) of one or more landmarks previously placed on the acetabular cup implant 216, to help orient the guide 426 into the predetermined relative guide/implant relationship with the stock prosthetic implant. This orientation between the guide 426 and the acetabular cup implant 216 may be especially important when the guide and acetabular cup implant are held relatively firmly to one another during their insertion to the surgical site.

The guides 426 in FIGS. 9 and 10 each are configured to substantially mate with a much smaller portion of the acetabular cup implant 216 than are the guides of FIGS. 4-8. The guide 426 of the fourth configuration, shown in FIG. 9, is shaped like a segment of a circle and may include one or more laterally oriented locating protrusions 538 that help steady and/or position the guide at a desired position on the acetabular cup implant 216. When present, the locating protrusions 538 may contact the acetabular cup implant 216 at a predetermined position to indicate that the guide 426 is placed correctly on the acetabular cup implant, which could include a structure (not shown) configured to engage with the locating protrusions. The guide 426 of FIG. 9 might be placed asymmetrically upon the acetabular cup implant 216, with the outer guide rim 848 being aligned with an outer rim of the acetabular cup implant.

Similarly to the guide 426 of FIG. 9, the guide 426 of the fifth configuration, shown in FIG. 10, is substantially shaped as a portion of a spherical shell and might be placed in any desired orientation on the acetabular cup implant 216 which would result in the desired fastener placement. As can be seen in FIG. 10, locating protrusions 538 may extend from any surface of the guide 426. For example, at least one locating protrusion 538 of FIG. 10 extends downward from the lower guide surface 528, toward the upper implant surface 222 when the guide 426 is mated with the acetabular cup implant 216. A locating protrusion 538 extending in this orientation may be configured to nest into a preselected one of the fastener apertures 220 to provide positive location and increased stability between the guide 426 and the acetabular cup implant 216.

Figure 11:
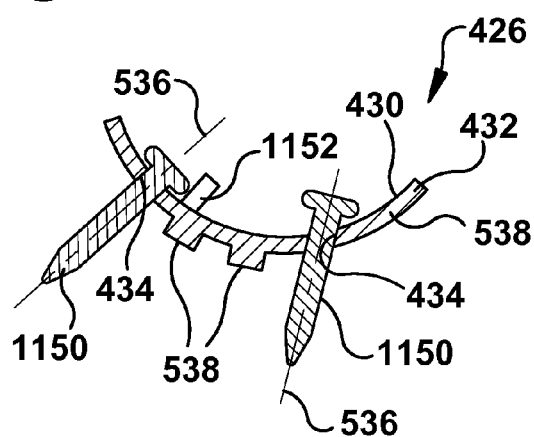
FIG. 11 is a schematic cross-sectional side view of the embodiment of FIG. 4 in any of the first through fifth configurations.

FIG. 11 illustrates, in schematic cross-section, an example of the guide 426 being used to define the predetermined target trajectories 536 and aperture locations, with fasteners 1150 being temporarily placed through selected ones of the guiding apertures 434 in FIG. 11 to show the target trajectories' role in guiding fasteners, be they screws, nails, brads, rods, or any other suitable fasteners. It is contemplated, though, that in most use environments, the guide 426 will be removed from the acetabular cup implant 216 before fasteners 1150 are installed on the acetabular cup implant.

It is apparent from FIG. 11 that the guide body 432 should be thick enough that each of the guiding apertures 434 can influence the trajectory of an elongate body passing therethrough. If the guide body 432 is too thin, the elongate body may precess within the guiding aperture 434 and deviate from the target trajectory 536. The elongate body intended for insertion through the guiding apertures 434 could be a fastener, a surgical tool, a guide pin, or any other suitable structure, and could be of any suitable size with respect to a corresponding guiding aperture 434 and/or fastener aperture 220. The elongate body could contact all, a portion of, or none of the inner walls of the guiding aperture 434 and/or fastener aperture 220, as desired.

At least one depth limiting feature 1152 may be provided to the guide 426 to limit further motion of the elongate body along the target trajectory and into the patient tissue past a predetermined depth. When the elongate body is a surgical tool, for example, the depth limiting feature 1152 may be a blocking stud, as shown in FIG. 11, which "catches" a drill chuck, a reamer shoulder, or another structure associated with the surgical tool when the surgical tool has reached the predetermined depth. It is contemplated that the depth limiting feature 1152 might be custom-designed and -manufactured for that particular patient tissue with the assistance of preoperative imaging. The depth limiting feature 1152 may also or instead be provided by the fastener 1150, such as, but not limited to, a head of the fastener having a diameter greater than the shaft and preventing the fastener head from passing through the fastener aperture 220—in this example, the depth limiting feature is the fastener head and may be adequately provided by a stock fastener.

Figure 12:
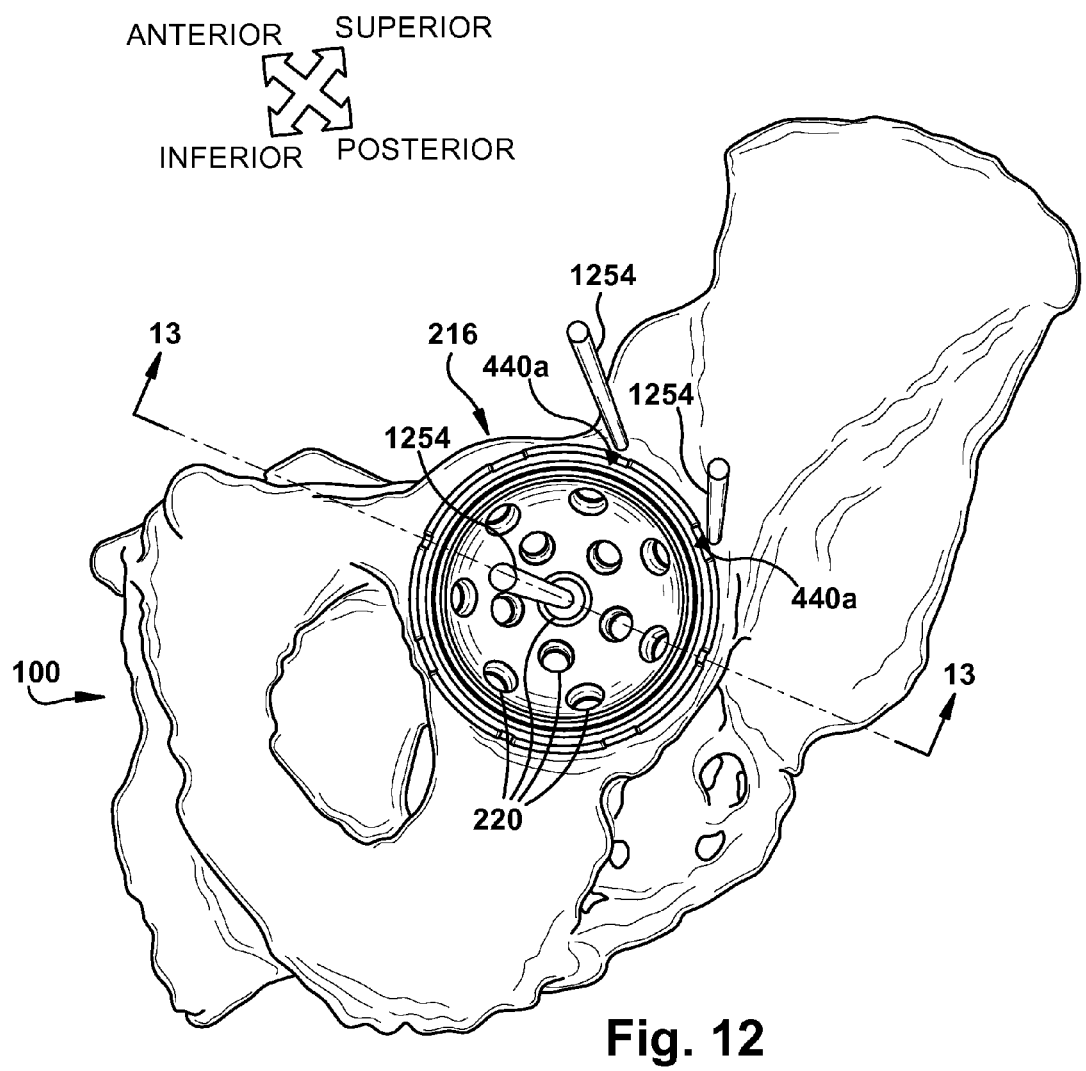
FIG. 12 is a top view of an example use environment for the embodiment of FIG. 4 as a prepared surgical site.
Figure 13:
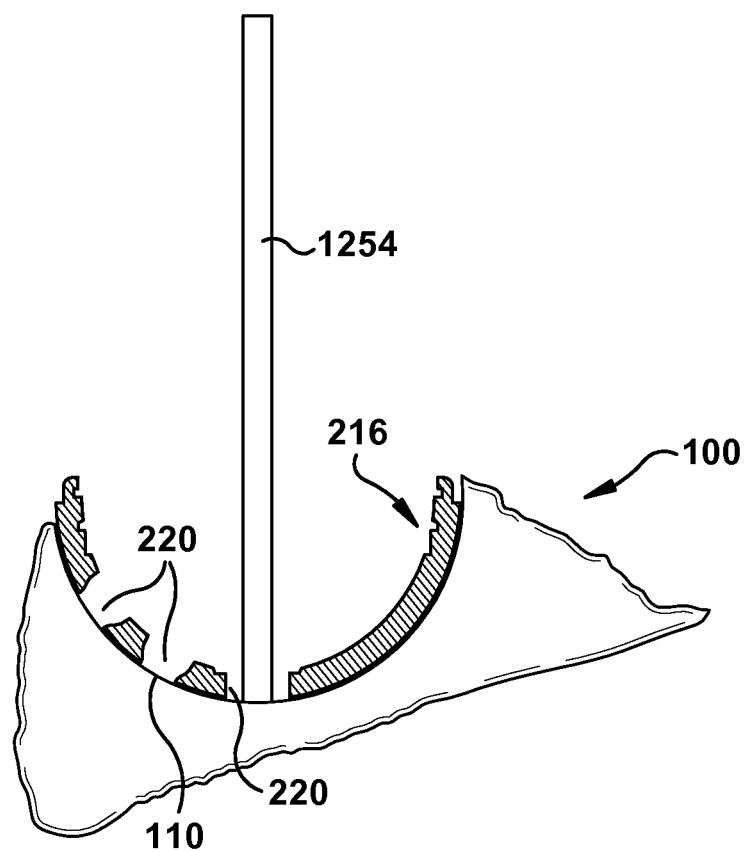
FIG. 13 is a cross-sectional view taken along line 13-13 of FIG. 12.

FIGS. 12-15 show top and cross-sectional side views of a portion of a surgical procedure in which the guide 426 may assist with providing target trajectories 536 and locations for fasteners 1150 to secure an acetabular cup implant 216 to an acetabulum 110. In FIGS. 12-13, the distal ends of three landmarks 1254 (shown here as guide pins) have been placed in the hip bone 100 in or near the acetabulum 110 (optionally with the assistance of a pin guide, not shown). The acetabular cup implant 216 has been placed in contact with a prepared acetabulum 110. Here, the acetabular cup implant 216 includes orienting features 440a to help the user rotationally orient the acetabular cup implant with the visual assistance of the two landmarks 1254 located outside the acetabulum 110 on the hip bone 100. The orienting features 440a might not be used for situations in which the acetabular cup implant 216 is rotationally symmetrical, but could be provided even with a symmetrical acetabular cup implant for any other desired reason.

Additionally, in FIGS. 12-13, a chosen one of the fastener apertures 220 of the acetabular cup implant 216 has been passed or slid over at least a portion of a landmark 1254 (which may be a central landmark, as shown) previously placed in the acetabulum 110 to help orient the acetabular cup implant within the acetabulum. Incidentally, this central landmark might have been used to help prepare the acetabulum 110, such as by guiding a reamer (not shown) to ream the acetabulum into a more standardized spherical shape to accept the stock acetabular cup implant 216. Optionally, this chosen one of the fastener apertures 220 may differ in size, shape, or any other characteristic from the other fastener apertures, to indicate and/or facilitate its use with the central landmark 1254. At the stage shown in FIGS. 12-13, the acetabular cup implant 216 is either sitting loosely in the acetabulum 110 or has a tenuous press-fit relationship with the acetabulum—in any case, there have been no fasteners 1150 installed, and the acetabular cup implant 216 is thus not yet a functional portion of a prosthetic hip joint.

Figure 14:
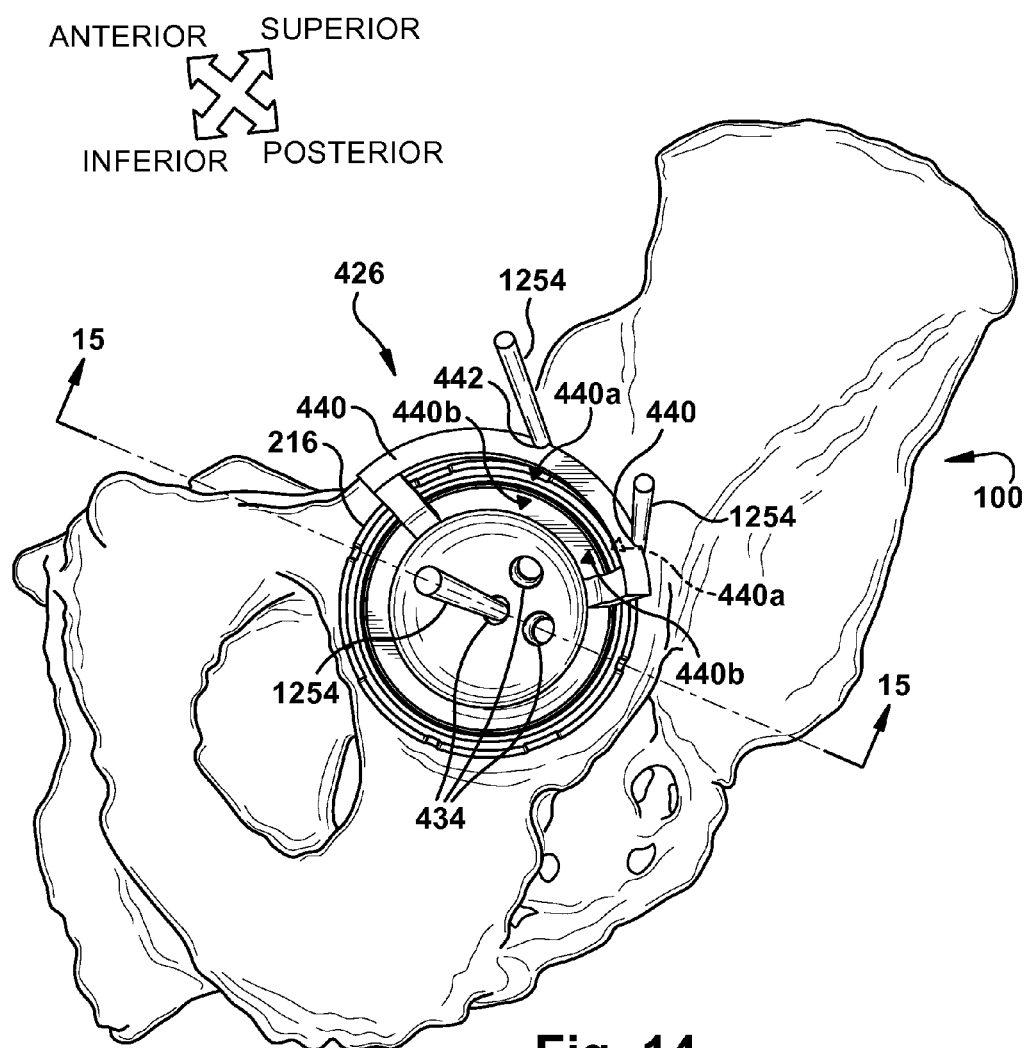
FIG. 14 is a top view of the example use environment of FIG. 12 with the addition of a schematic top view of the embodiment of FIG. 4.
Figure 15:
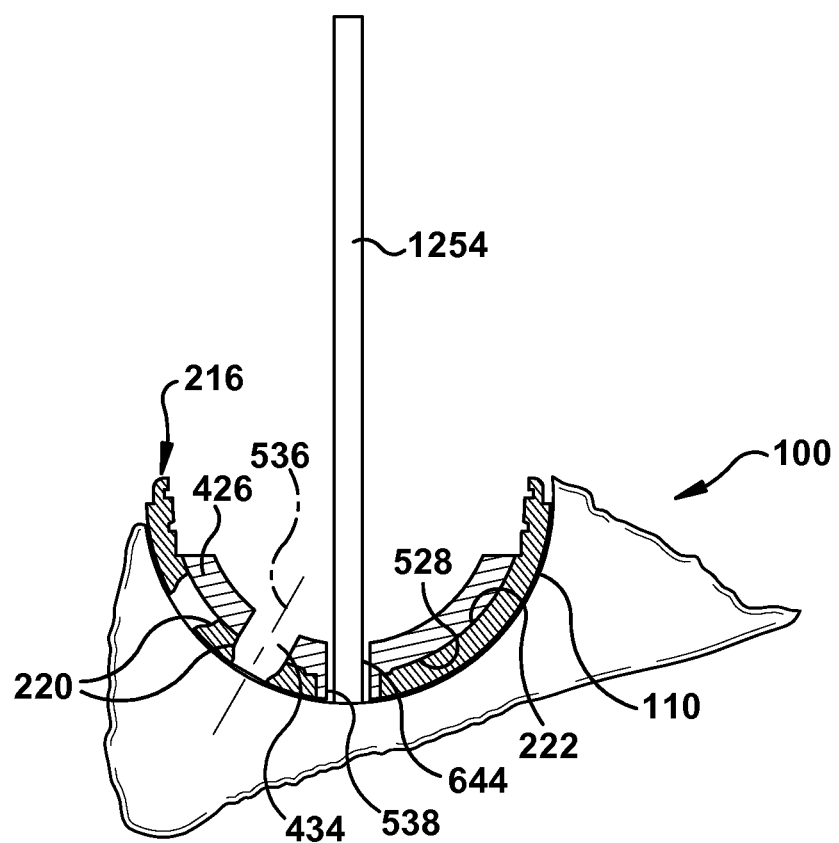
FIG. 15 is a cross-sectional view taken along line 15-15 of FIG. 14.

FIGS. 14-15 show the hip bone 100 and acetabular cup implant 216 of FIGS. 12-13 with the addition of an overlying guide 426 according to the present invention. Similar to the orientation of the acetabular cup implant 216, the guide 426 in FIGS. 14-15 has a guiding aperture 434 which been passed or slid over at least a portion of the central landmark 1254 previously placed in the acetabulum 110 to help achieve a predetermined guide orientation within the acetabular cup implant. The guide 426, as shown, includes inscribed orienting features 440b (to distinguish from the orienting features 440a of the acetabular cup implant 216) which help rotationally orient the acetabular cup implant with the assistance of the two landmarks 1254 located outside the acetabulum 110 on the hip bone 100. The guide 426 of FIGS. 14-15 also includes a bridge-like orienting feature 440 including orienting indicators 442 which are in the signaling relationship with two of the landmarks 1254 in the pictured view. Optionally and as previously discussed, at least a portion of the bridge-like orienting feature 440 could include a shaped profile (not shown) which achieves the signaling relationship through mating with a preselected portion of the patient tissue.

The stock acetabular cup implant 216 has a predetermined number of fastener apertures 220, at least one of which may be extraneous, as previously discussed. The guide 426 also has a predetermined number of guiding apertures 434, which may be any number, but is contemplated to be no more than the predetermined number of fastener apertures 220 in the acetabular cup implant. At least one guiding aperture 434 should be collinear or otherwise coincident in some physical property with a predetermined one of the fastener apertures 220. In this manner, the guide 426 acts as a "mask" to obscure those fastener apertures 220 which are not predetermined to receive a fastener 548, while providing a location and target trajectory 536 for installation of fasteners 1150 into those fastener apertures which are to be used in securing the acetabular cup implant 216 to the hip bone 100.

As is apparent from the cross-sectional view of FIG. 15, the locating protrusions 538 on the underside of the guide 426 each nest into preselected ones of the fastener apertures 220 to help provide positive locating and stabilizing features to the guide 426. Regardless of the presence of locating protrusions 538, however, it is contemplated that at least a portion of the guide 426 will be in contact with the acetabular cup implant 216 in a predetermined orientation when the structures have achieved the configuration shown in FIGS. 14-15. The locating protrusion 538 shown in FIG. 15 nests into a central one of the fastener apertures 220, which also holds a central landmark 1254. Accordingly, this locating protrusion 538 doubles as a guiding aperture 434 and can accept a fastener or other structure inserted thereinto.

One example sequence of use for any configuration of the first embodiment of the present invention is shown in FIGS.

Figure 16:
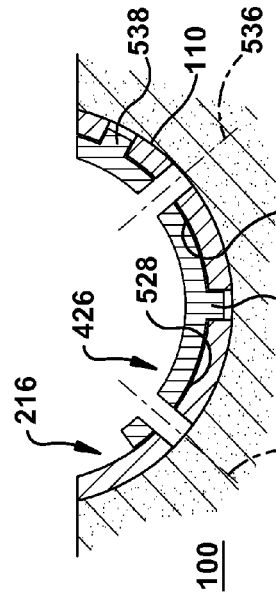
FIGS. 16-21 are schematic cross-sectional views of a sequence of operation of the embodiment of FIG. 4.

16-21. In FIG. 16, the acetabular cup implant 216 has been placed in the acetabulum 110. It should be understood that the acetabular cup implant 216 is not necessarily in the predetermined implant orientation at this point in the procedure. The guide 426 is then placed atop the acetabular cup implant 216 with the lower guide surface 528 in mating contact (optionally with the assistance of one or more locating protrusions 538) with the upper implant surface 222 in the predetermined relative guide/implant orientation.

The guide 426 and the acetabular cup implant 216 are then shifted as desired, independently or concurrently and optionally with the use of one or more orienting features 440 and/or orienting indicators 442, as described above with reference to FIGS. 4-8, until the acetabular cup implant is in the predetermined implant orientation and the guide is in a predetermined guide orientation. This view is shown in FIG. 17.

Figure 18:
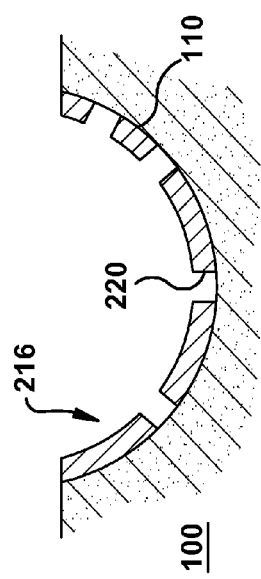
Figure 20:
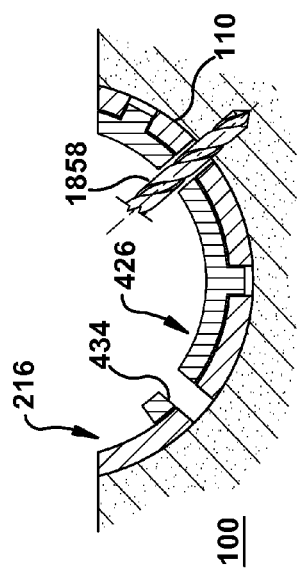
Figure 17:
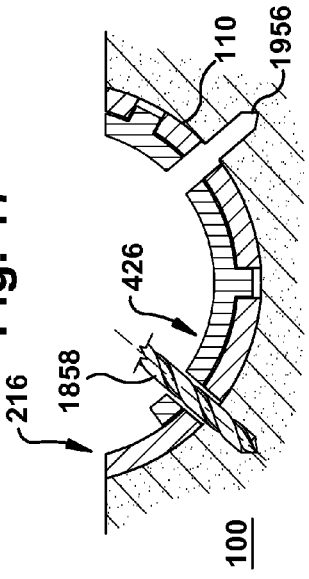
Figure 19:
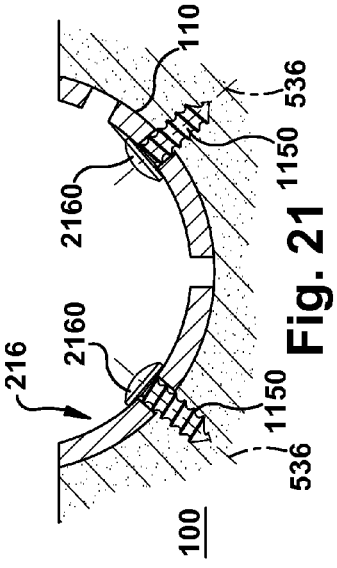

Once the acetabular cup implant 216, guide 426, and acetabulum 110 have achieved the relative positioning and configuration shown in FIG. 17, the user can prepare for installation of the fasteners 1150 in the preselected aperture locations (indicated by the placement of the guiding apertures 434 on the guide) and along the target trajectories 536. For example, when fastener cavities 1956, pilot or otherwise, are to be pre-drilled to receive the fasteners 548, at least one guiding aperture 434 may be configured to guide a surgical tool 1858 through a corresponding fastener aperture 220 and into the patient tissue along the target trajectory 536 to create the fastener cavity in the patient tissue, as shown in FIGS. 18-20. Though omitted here for clarity, a guiding sleeve (not shown) may be placed into the guiding aperture 434 (and optionally extend into the corresponding fastener aperture 220) to protect the guide 426 and/or the acetabular cup implant 216 from the forces (e.g., rotational) exerted by the surgical tool 1858. When present, the guiding sleeve may also serve as an extension of the guiding aperture 434 to emphasize the target trajectory 536 and help maintain collinearity of the fastener cavity 1956 with the target trajectory. As another example, not shown, when the fastener 1150 does not require a pre-drilled hole (e.g., the fastener is a self-tapping screw or a nail), at least one guiding aperture 434 may be configured to guide the fastener itself through a corresponding fastener aperture 220 and into the patient tissue along the target trajectory 536 into the final arrangement of FIG. 21.

Figure 21:
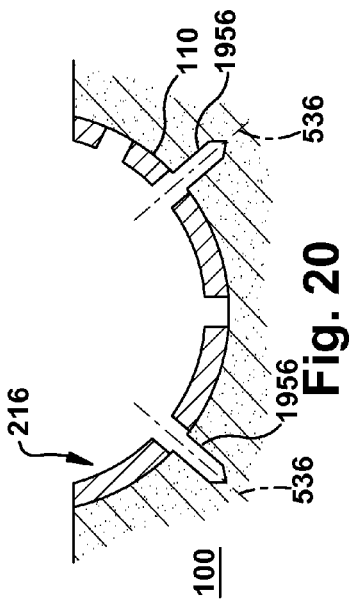

In the former arrangement (i.e., guide 426 guides surgical tool 1858), the guide may be removed from the acetabular cup implant 216 once the fastener cavities 1956 are produced, such as in FIG. 20. The acetabular cup implant 216 is maintained in place while fasteners 1150 are then installed directly through the selected fastener apertures 220 (i.e., those with associated fastener cavities already drilled) to secure the acetabular cup implant to the acetabulum 110, forming the final arrangement shown in FIG. 21. Optionally, the fastener apertures 220 may be countersunk (not shown) to accommodate each fastener head 2160 within the material of the acetabular shell 218 and present a substantially smooth upper implant surface 222. Alternately or additionally, at least one fastener head 2160 could remain protruding from the acetabular shell 218 above the upper implant surface 222, as shown in FIG. 21, particularly if such would be desirable in attaching another prosthetic implant structure (e.g., an acetabular liner, not shown) to the acetabular cup implant 216. As other options, the fasteners 1150 could be substantially headless or could have fastener heads 2160 which interact with the inner surface of the fastener apertures 220 to remain recessed below the upper implant surface 222 while still providing a securing function to the acetabular cup implant 216.

In the latter arrangement (i.e., guide 426 guides fastener [s] 1150), the guide may be configured to accommodate the fastener heads 2160, if any, before the guide is removed from the acetabular cup implant 216. For example, the guide 426 could be frangible and thus equipped for at least partial disassembly and removal when the fasteners 1150 have been substantially guided along the target trajectories 536. As another example, the guiding apertures 434 could be elongate and configured to create a slot open to the lateral edge of the guide body 432, so that the guide 426 can be moved laterally out of engagement with the acetabular cup implant 216 without changing the trajectories of the partially-inserted fasteners 1150 from the target trajectories 536. Regardless of the operation or structure employed, at least one of the guiding apertures 434, fastener apertures 220, and fasteners 1150 could be configured to allow removal of the guide 426 from the acetabular cup implant 216, again without changing the trajectories of the partially-inserted fasteners from the target trajectories 536. When the fasteners 1150 are left partially inserted at the time the guide 426 is removed, the user may complete their insertion without the guiding influence of the guide; it will generally be desirable, however, that the guide not be removed until there is substantial certainty that the fasteners are adequately engaged with the patient tissue of the hip bone 100 and will continue to follow their target trajectories 536 during the remaining insertion operation even without the guide being present.

Regardless of the way in which the guide 426 is removed, the acetabular cup implant 216 is anticipated to be securely fastened to the acetabulum 110 at, or shortly after, the guide removal is accomplished. The user may then continue with the surgical processes to complete the installation of the prosthetic implant and to conclude the surgical procedure as desired.

In summary, the guide 426 can assist the user with placement of fasteners 1150 into a prosthetic implant and a patient tissue in a desired fashion by providing target trajectories 536 and aperture (that is, insertion) locations for each fastener. Each target trajectory 536 and each aperture location is preselected responsive to preoperative imaging of the patient tissue, with each target trajectory and each aperture location being preselected to facilitate placement of a fastener 1150 into a stock prosthetic implant and the underlying patient tissue at a preselected fastener location and a preselected fastener trajectory before and/or after removal of the guide 426 from the stock prosthetic implant. The guide 426 also may be configured to enter a predetermined orienting relationship, such as with the assistance of an orienting feature 440, with a natural or acquired landmark (not shown), such as a guide pin, wire, marking, and/or other location indicator previously placed in a predetermined relationship with the patient tissue, to facilitate correct location of at least one target trajectory 536 with respect to the patient tissue.

Figure 23:
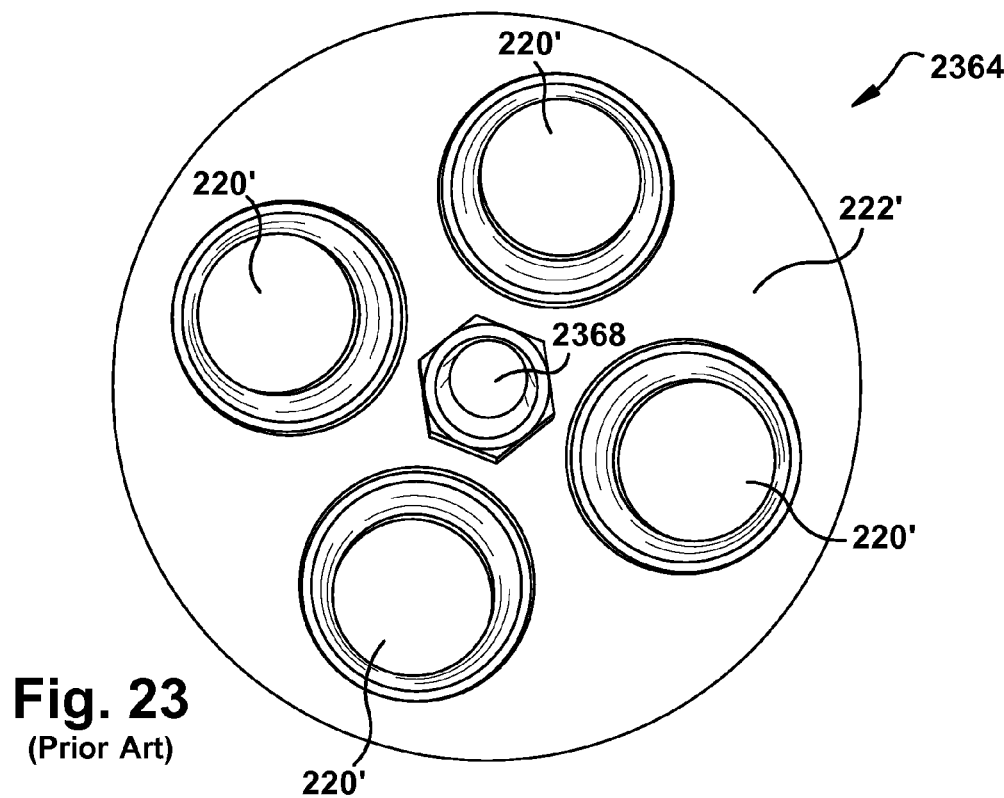
FIG. 23 is a top view of a second prior art prosthetic component.
Figure 24:
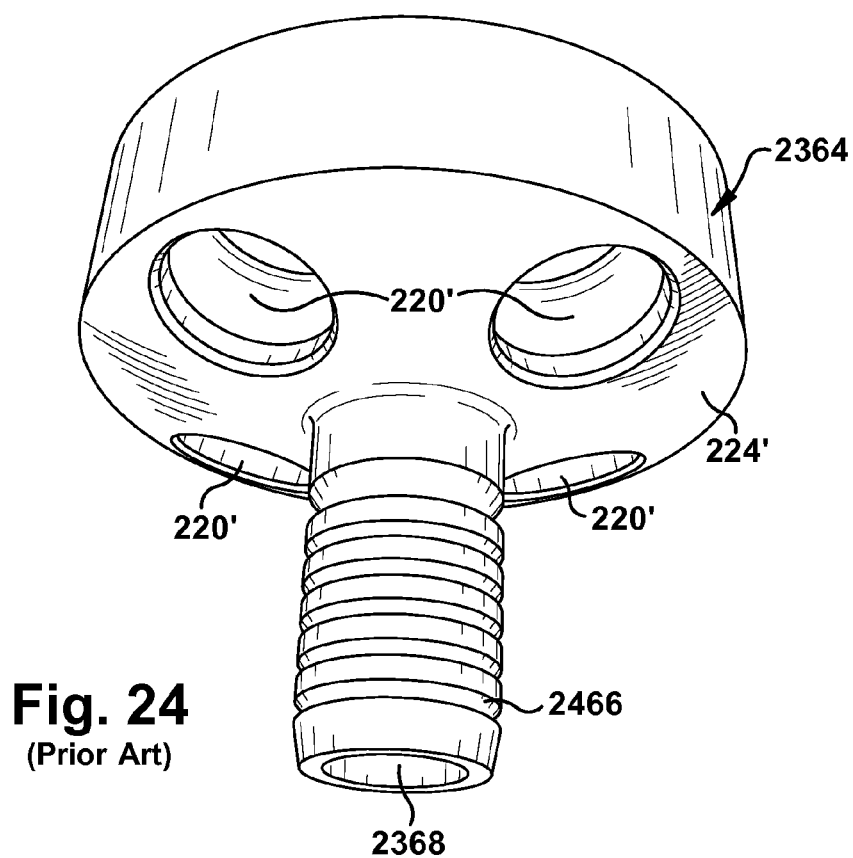
FIG. 24 is a side view of the prior art prosthetic component of FIG. 23.
Figure 25:
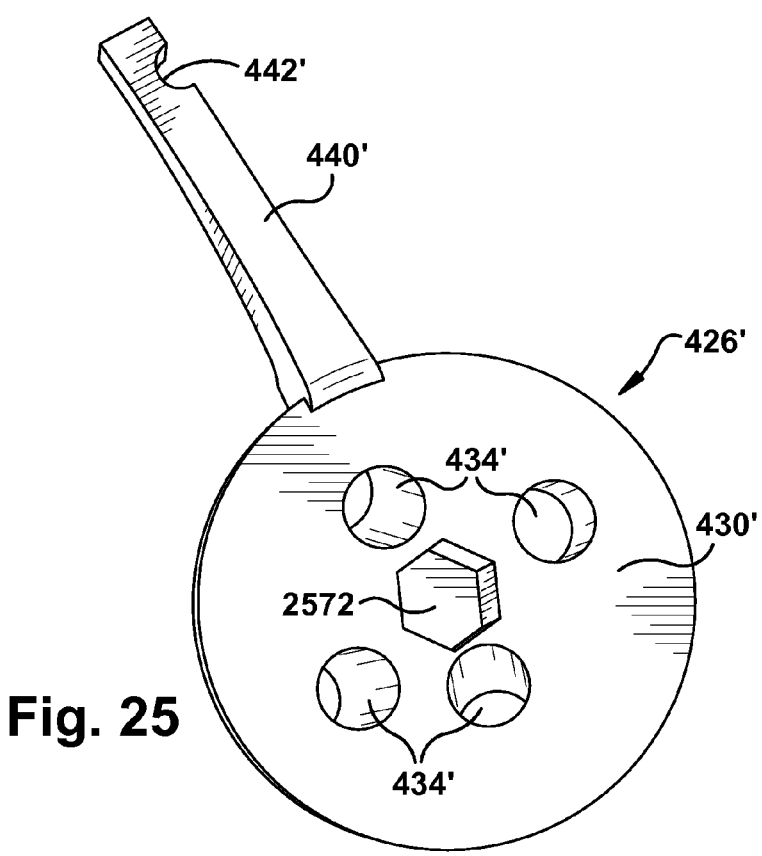
FIG. 25 is a top view of a second embodiment of the present invention.
Figure 26:
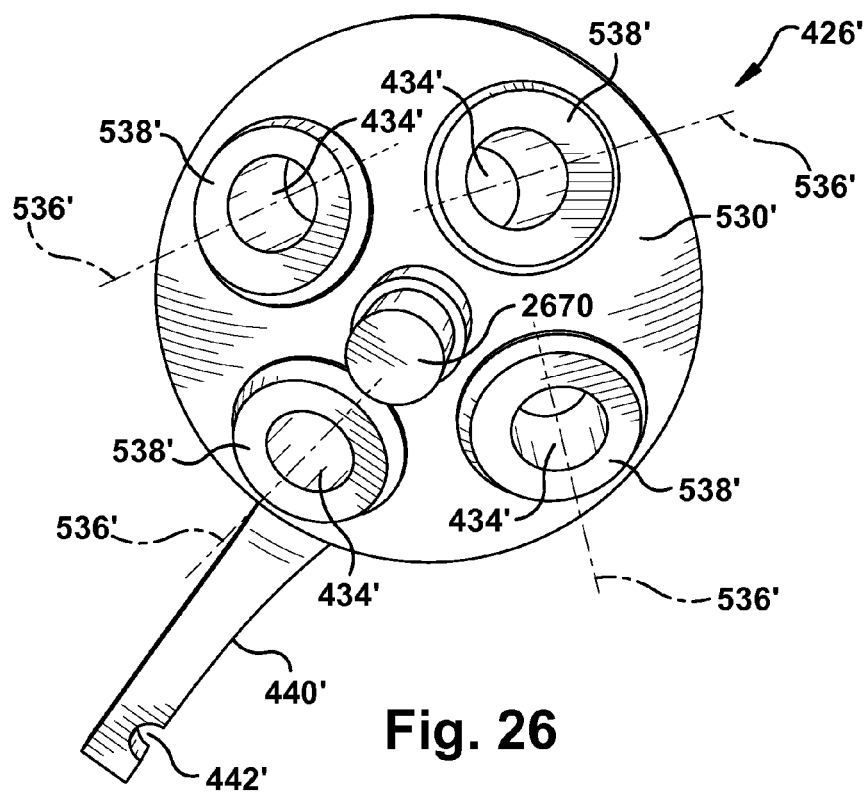
FIG. 26 is a bottom view of the embodiment of FIG. 25.
Figure 27:
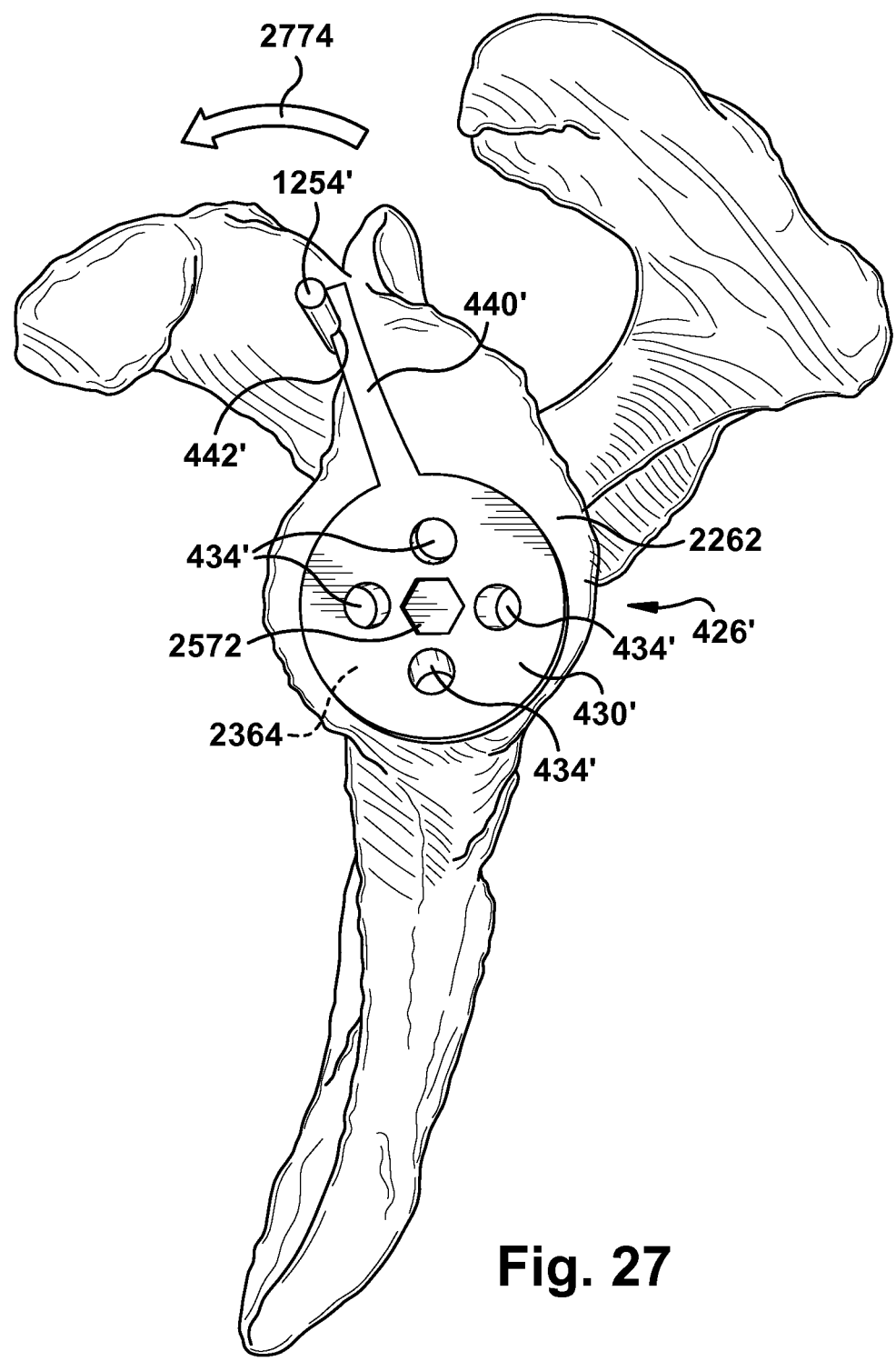
FIG. 27 is a perspective view of the embodiment of FIG. 25 in the second example use environment of FIG. 22.

FIGS. 22-27 depict a guide 426' according to a second embodiment of the present invention and related structures. The guide 426' of FIGS. 25-27 is similar to the guide 426 of FIGS. 4-10 and therefore, structures of FIGS. 25-27 that are the same as or similar to those described with reference to FIGS. 4-10 have the same reference numbers with the addition of a "prime" mark. Description of common elements and operation similar to those in the previously described first embodiment will not be repeated with respect to the second embodiment.

Figure 22:
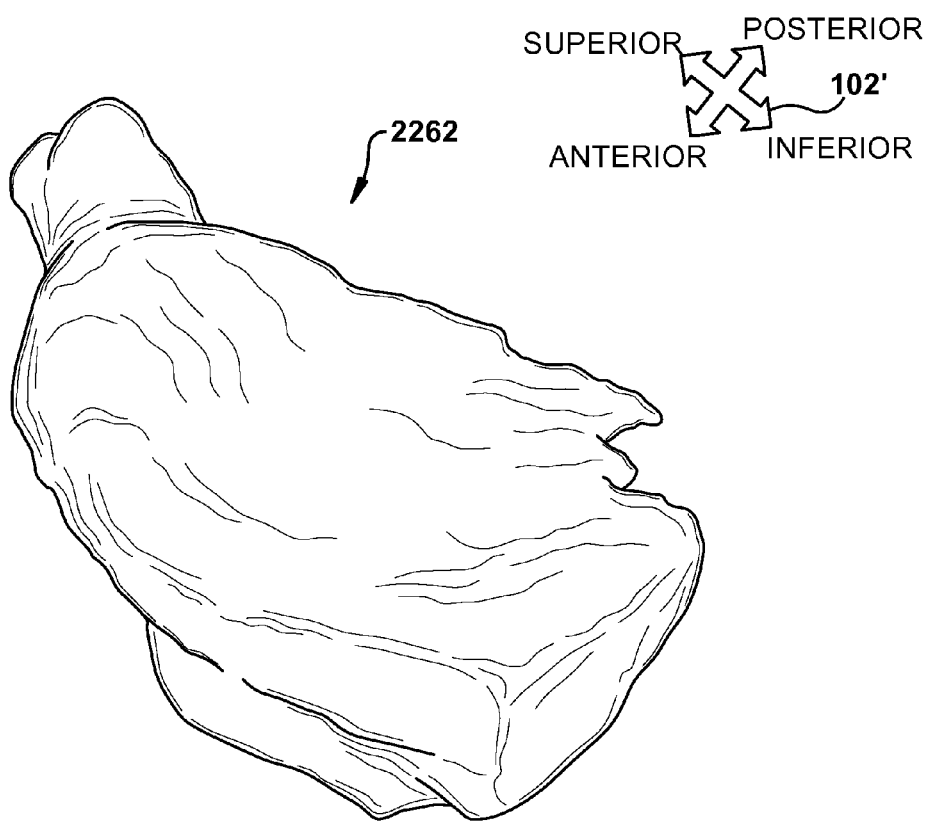
FIG. 22 is a top view of a second example use environment.

FIG. 22 is a partial perspective view of the scapula, with particular emphasis on the glenoid fossa 2262. A glenoid implant 2364, shown in FIGS. 23-24, is the stock prosthetic implant for use with a prosthetic shoulder replacement surgery for the second embodiment of the present invention. This glenoid implant 2364 happens to be a metaglene implant, which accepts a glenosphere component (not shown) in a known manner for a reverse shoulder prosthesis. The glenoid implant 2364 includes a lower implant surface 224', an upper implant surface 222', and a plurality of fastener apertures 220' extending between the lower and upper implant surfaces. Certain configurations of the glenoid implant 2364 may also include an implant shaft 2466.

During installation of the glenoid implant 2364, a shaft aperture (not shown) is drilled into the patient tissue (here, the patient's glenoid fossa 2262) and the implant shaft 2466 is placed in the shaft aperture for initial securement and stabilization before the fasteners 1150' are installed. The implant shaft 2466 may act as a pivot point for rotation of the glenoid implant 2364 during movement of the glenoid implant into the predetermined implant orientation, similar to the procedure described above for the first embodiment. In this situation, the shaft aperture serves as a landmark 1254' to communicate pre-operatively planned location information to the user during the surgical procedure. The implant shaft 2466 may also act to help stabilize the glenoid implant 2364 on an ongoing basis, after conclusion of the described surgical procedure. The glenoid fossa 2262 could be reamed, cut, grafted, or otherwise altered from its native or pathologic state to accept the glenoid implant 2364, as desired according to the preoperative plan and/or an intra-operative decision.

Optionally, a landmark 1254' such as the previously described guidewire may be passed through the glenoid implant 2364 and into the patient tissue of the glenoid fossa 2262 through the use of a shaft aperture 2368 passing through the implant shaft 2466. When the shaft aperture 2368 is used in this manner, the landmark 1254' may be placed first, to help locate the glenoid implant 2364 upon the glenoid fossa 2262, or the landmark may be placed into a glenoid implant already in place on the glenoid fossa, to help with location of the guide 426' upon the glenoid implant.

The desire for use of one or more landmark(s) 1254' and/or guide(s) 426' for the shoulder use environment stems from the relatively open plateau of the glenoid fossa 2262, on which the glenoid implant 2364 can be positioned and oriented a number of different ways. In contrast, the acetabulum 110 tends to naturally cup and settle an appropriately sized acetabular cup implant 216, inserted by a knowledgeable user, into one of a few positions, and the rotational orientation of the acetabular cup implant can then be refined through use of the orienting feature(s) 440, when present. Particularly in a revision situation, due to anatomic abnormalities, it may be difficult to position either of these components in the glenoid fossa 2262 or acetabulum 110, as the case may be. This difficulty generally stems from bone loss or surgical alteration of the patient tissue resulting in a loss of natural landmarks.

A guide 426' for use with the glenoid implant 2364 is shown in FIGS. 25-27. As can be seen in FIG. 26, the guide 426' includes a central protrusion 2670 configured to nest into the shaft aperture 2368 of the glenoid implant 2364. In the second embodiment, the fastener apertures 220' of the glenoid implant 2364 also serve to accept the locating protrusions 538' of the guide 426', which surround each of the fastener apertures, as shown. The fastener apertures 220' are optionally countersunk to accept the locating protrusions 538'. When a countersunk fastener aperture 220' is provided for a locating protrusion 538', whether the countersunk feature is added by the user or originally provided by the implant manufacturer, the countersunk portion might also or instead be used to accept a fastener head 2160' to provide a smooth upper implant surface 222' with no protruding fastener heads when securement of the glenoid implant 958 to the patient tissue is complete. With reference to FIG. 26, the guiding apertures 434' each can be seen to be located on the lower guide surface 528' in a position coincident with the fastener apertures 220' on the upper implant surface 222' when the guide 426' is mated with the glenoid implant 2364 as shown in FIG. 27 (in this Figure, the glenoid implant is located directly underneath the guide 426', as indicated by the dashed leader line). However, as can be seen in FIGS. 25 and 27, the location of the fastener apertures 220' upon the upper guide surface 430' is dictated by the target trajectory 536' defined by each fastener aperture and is patient-specific, being preselected responsive to preoperative imaging of the patient tissue.

An optional handling feature 2572 is indented into the upper guide surface 430' and is configured as a connection point for a handling tool (not shown), which may provide assistance with moving the guide 426' within the surgical field. Because the handling feature 2572 shown in the figures is located collinearly with the implant shaft 2466, the handling tool can be used to rotate the guide 426' about an axis defined by the implant shaft—this axis, when present, is acting as a landmark 1254' by indicating information to the user regarding a pre-planned location of the surgical site. While the handling feature 2572 shown is a void adapted to receive a hex-head driver, any suitable handling feature may protrude from, and/or be recessed into, any surface of the guide 426' and may have any desired shape or configuration. Sometimes the available maneuvering space in a surgical field is relatively restricted, and it may be useful for a forceps, hex wrench (perhaps with a frictional fit or other feature to nest into the handling feature 2572), Kocher tool, hemostat, or other user-manipulated handling tool (not shown) to selectively interact with the handling feature to hold the guide 426' steady and/or to move the guide to a desired position. One or more features, such as indents, apertures, cavities, lugs, undercuts, or any other suitable structures could be provided to the handling feature 2572 or to any other structure of the guide 426' to facilitate gripping of the guide by any handling tool, in general, and/or by a particular handling tool.

In use, the guide 426' of the second embodiment operates similarly to the guide 426 of the first embodiment. The glenoid implant 2364 of FIGS. 23-24 is placed upon the glenoid fossa 2262 surface. Optionally, an implant-receiving aperture (not shown) may have been previously drilled in the glenoid fossa 2262 surface—if so, the implant shaft 2466 is inserted into the implant-receiving aperture as a part of placing the lower implant surface 224' in contact with the patient tissue. The guide 426' is placed atop the glenoid implant 2364 with the lower guide surface 528' in contact with the upper implant surface 222'. When present, the locating protrusions 538' of the guide 426' may mate with the fastener apertures 220' of the glenoid implant 2364.

Once the glenoid implant 2364 and guide 426' are mated together in the predetermined relative guide/implant orientation atop the glenoid fossa 2262 surface, the glenoid implant and guide can be moved concurrently to move both the guide and the glenoid implant into predetermined guide and implant orientations with respect to the glenoid surface. In other words, engagement between the guide 426' and the glenoid implant 2364 causes forces exerted upon the guide to be transferred to the glenoid implant, and the user can move both the glenoid implant and the guide concurrently by moving just the guide. For example, and presuming that the glenoid implant 2364 includes an implant shaft 2466 received into an implant-receiving aperture in the glenoid fossa 2262 surface, a clockwise force (indicated by clockwise arrow 2774 in FIG. 27) exerted upon the orienting feature 440' will pivot the guide 426'—and thus the mated glenoid implant—about the implant shaft.

The guide 426' and mated glenoid implant 2364 may be rotated, for example, until the orienting indicator 442' achieves a predetermined signaling relationship with a landmark 1254' such as the depicted guide pin. Accordingly, the guide 426' can rotate the glenoid implant 2364 into a predetermined implant orientation with respect to the glenoid fossa 2262 surface. As another example, the guide 426' and mated glenoid implant 2364 could be placed with the orienting indicator 442' at, or close to, the predetermined signaling relationship with the landmark 1254' before the glenoid implant comes into contact with the glenoid fossa 2262. In this latter situation, the glenoid implant 2364 could be guided into the predetermined implant orientation concurrently with being brought into contact with the glenoid fossa 2262 as the orienting indicator 442' slides along the length of the guide pin via a rail-like dynamic guiding technique Once the guide 426' is mated to the glenoid implant 2364 and the orienting feature 440' has been rotated or otherwise moved into the predetermined orienting relationship with the previously placed landmark 1254, the glenoid implant will have achieved the predetermined implant orientation. The desired fastener 1150' locations with respect to the glenoid fossa 2262 surface will correspond to one or more of the fastener apertures 220' of the glenoid implant 2364 when the glenoid implant has reached the predetermined implant orientation. A surgical tool 1858' and/or fasteners 1150' can then be guided along the target trajectories 536' by the guide 426' through the fastener apertures 220', the guide 426' can be removed at an appropriate stage in the glenoid implant 2364 securement procedure, and installation of the glenoid implant and the remainder of the prosthetic shoulder assembly can then proceed apace.

Figures 28, 29:
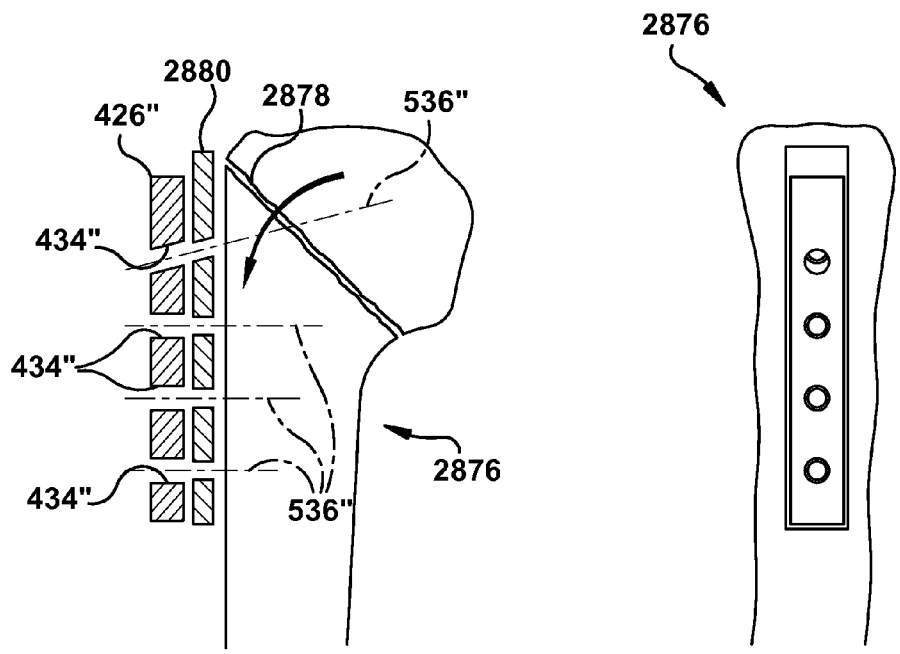
FIG. 28 is a schematic side view of a third embodiment of the present invention in an example use environment.
FIG. 29 is a front view of the embodiment of FIG. 28.

FIGS. 28-29 depict a guide 426" according to a third embodiment of the present invention. The guide 426" of FIGS. 28-29 is similar to the guide 426 of FIGS. 4-10 and therefore, structures of FIGS. 28-29 that are the same as or similar to those described with reference to FIGS. 4-10 have the same reference numbers with the addition of a double "prime" mark. Description of common elements and operation similar to those in the previously described first and second embodiments will not be repeated with respect to the third embodiment.

In FIGS. 28-29, a patient tissue (here, a long bone 2876) having a malunion problem has previously been resected, optionally with the assistance of an aid such as the aforementioned guide disclosed in co-pending U.S. patent application Ser. No. 13/282,509, filed Oct. 27, 2011, titled "System and Method for Association of a Guiding Aid with a Patient Tissue" and claiming priority to U.S. Provisional Patent Application No. 61/408,359, filed Oct. 29, 2010 and titled "System and Method for Association of a Guiding Aid with a Patient Tissue", the entire contents of both of which are incorporated herein by reference. The resected tissue has been removed, and the long bone 2876 has been collapsed along the resection line 2878. A stock prosthetic implant, shown here as bone plate 2880, has been placed in a predetermined implant orientation with respect to the long bone 2876. A guide 426" has been placed into a predetermined guide/implant orientation with respect to the bone plate 2880. The guide 426" includes at least one guiding aperture 434" at a predetermined aperture location, the guiding aperture(s) 434" each defining a target trajectory 536. After achieving the positioning shown in the Figures, the guide 426" is used to aid with the attachment of the bone plate 2880 to the long bone 2876 in a manner analogous to those described above with reference to the first and second embodiments of the present invention.

The above description presumes that the guide 426 is removed from the prosthetic implant component before completion of the surgery. It is contemplated, nevertheless, that the guide 426 and/or a stock prosthetic implant component could be configured for maintenance of the guide within the body, perhaps as a part of the completely installed prosthetic implant structure. One way in which this might be accomplished, using as an example the aforementioned acetabular cup implant 216, is for the fastener apertures 220 to be located in an area of the acetabular shell 218 which has a recessed upper implant surface 222 to accept the guide 426 in a manner which results in a substantially even-profiled composite inner shell surface for smooth contact with the femoral implant component, this composite inner shell surface being comprised of the upper implant surface in combination with the upper guide surface 430.

It is contemplated that the guide 426 could be used with an instrument or related components such as those disclosed in co-pending U.S. patent application Ser. No. 13/282,495, filed Oct. 27, 2011, titled "System and Method for Assisting with Attachment of a Stock Instrument with Respect to a Patient Tissue" and claiming priority to U.S. Provisional Patent Application No. 61/408,376, filed Oct. 29, 2010 and titled "System and Method for Assisting with Arrangement of a Stock Instrument with Respect to a Patient Tissue", the entire contents of both of which are incorporated herein by reference.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the guide 426 are merely illustrative; one of ordinary skill in the art could readily determine any number of tools, sequences of steps, or other means/options for placing the above-described apparatus, or components thereof, into positions substantially similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for most applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. An adhesive (such as, but not limited to, bone cement) could be used in conjunction with the system and method described herein. The guide 426 may include a plurality of structures cooperatively forming the base body and temporarily or permanently attached together in such a manner as to permit relative motion (e.g., pivoting, sliding, or any other motion) therebetween. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A sleeve (not shown) could be provided to surround the fastener 1150 and/or surgical tool 1858 during insertion into at least one of the guiding aperture 434 and the fastener aperture 220—the sleeve (when present) could extend at least partially into the guiding aperture and/or the fastener aperture, and the sleeve could have variable wall thickness about a circumference thereof in order to place the elongate body in an offset relationship with a centerline of the relevant aperture(s). An adhesive (such as, but not limited to, bone cement) could be used in conjunction with the system and method described herein. Any of the components described herein could have a surface treatment (e.g., texturization, notching, etc.), material choice, and/or other characteristic chosen to provide the component with a desired interaction property (e.g., tissue ingrowth, eluting of a therapeutic material, etc.) with the surrounding tissue. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A system including a guide and a stock prosthetic implant, the guide adapted to with attachment of the stock prosthetic implant to a patient tissue, the guide comprising:
   a lower guide surface configured to contacting an upper implant surface of the stock prosthetic implant when a lower implant surface of the stock prosthetic implant is in contact with the patient tissue, at least a portion of the lower guide surface being contoured to substantially mate with at least a portion of the upper implant surface, and
   wherein both the lower guide surface and the upper implant surface are concave in profile;
   an upper guide surface spaced longitudinally apart from the lower guide surface by a guide body, the upper guide surface being accessible to a user when the lower guide surface is in contact with the upper implant surface;
   wherein both the upper guide surface and the lower implant surface are convex in profile;
   at least one guiding aperture extending through the guide body between the upper and lower guide surfaces at a predetermined aperture location with respect to the guide body, the at least one guiding aperture defining a predetermined target trajectory through the guide body, and the at least one guiding aperture configured to be collinear with a corresponding one of a plurality of fastener apertures in the stock prosthetic implant when the lower guide surface is mated with the upper implant surface; and
   two or more locating protrusions integrally formed with the guide body, the two or more locating protrusions extending from the lower guide surface of the guide body toward the upper implant surface for engaging the upper implant surface, the two or more locating protrusions being spaced apart from the at least one guiding aperture, the two or more locating protrusions being configured to nest into preselected ones of the fastener apertures of the stock prosthetic implant, wherein the guide is configured to be engaged engages in a fixed rotational orientation relationship with the stock prosthetic implant when the two or more locating protrusions are nested with the preselected ones of the fastener apertures, and wherein relative rotation between the guide and the stock prosthetic implant is prevented in said fixed rotational orientation relationship;
   wherein at least one of the target trajectory and the aperture location of each guiding aperture is preselected responsive to preoperative imaging of the patient tissue.

2. The guide of claim 1, wherein the guide includes a number of guiding apertures which is no more than the number of fastener apertures, each guiding aperture being collinear with a predetermined one of the fastener apertures when the lower guide surface is mated with the upper implant surface.

3. The guide of claim 1, wherein at least one guiding aperture is configured to guide a surgical tool through a corresponding fastener aperture and into the patient tissue along the target trajectory to create a fastener cavity in the patient tissue.

4. The guide of claim 3, including at least one depth limiting feature configured to prevent further motion of at least one of a fastener and the surgical tool along the target trajectory and into the patient tissue past a predetermined depth.

5. The guide of claim 1, wherein the upper guide surface includes at least one orienting feature, the orienting feature being configured to guide the user in placing the guide in a predetermined relative guide/implant orientation with the stock prosthetic implant.

6. The guide of claim 1, being at least one of custom manufactured and modified from a stock guide, responsive to at least one of preoperative imaging of the patient tissue and preoperative selection of the stock prosthetic implant.

7. The guide of claim 1, wherein each target trajectory and each aperture location is preselected responsive to preoperative imaging of the patient tissue, with each target trajectory and each aperture location being preselected to facilitate placement of a fastener into the stock prosthetic implant and the underlying patient tissue at a preselected fastener location and a preselected fastener trajectory after removal of the guide from the stock prosthetic implant.

8. The guide of claim 1, including an orienting feature, the orienting feature entering a predetermined orienting relationship with a previously placed landmark while the lower guide surface is in mating contact with at least a portion of the upper implant surface in a predetermined relative guide/implant orientation.

9. The guide of claim 8, wherein the orienting feature includes an orienting indicator, and the orienting indicator achieves a predetermined signaling relationship with the landmark while the guide and stock prosthetic implant are in the predetermined relative guide/implant orientation.

10. The guide of claim 8, wherein the stock prosthetic implant and the guide are moved concurrently to move both the guide and stock prosthetic implant into predetermined guide and implant orientations with respect to the patient tissue.

11. The guide of claim 10, wherein the stock prosthetic implant and the guide are rotatable concurrently when engaged in said fixed rotational orientation relationship, to rotate both the guide and the stock prosthetic implant into the predetermined guide and implant orientations with respect to the patient tissue.

12. A system including a guide and a stock prosthetic implant, the guide adapted to assist with attachment of the stock prosthetic implant to a patient tissue, the guide comprising:
 a lower guide surface contacting an upper implant surface of the stock prosthetic implant when a lower implant surface of the stock prosthetic implant is in contact with the patient tissue, the lower guide surface being contoured to substantially mate with at least a portion of the upper implant surface, and wherein both the lower guide surface and the upper implant surface are concave in profile,
 an upper guide surface spaced longitudinally apart from the lower guide surface by a guide body, the upper guide surface being accessible to a user when the lower guide surface is in contact with the upper implant surface; wherein both the upper guide surface and the lower implant surface are convex in profile; and
 two or more locating protrusions integrally formed with the guide body of the guide and extending from the lower guide surface toward the stock prosthetic implant for engaging an upper surface of the stock prosthetic implant, the two or more locating protrusions nest into respective two or more corresponding fastener apertures in the stock prosthetic implant, the two or more location protrusions of the guide being spaced apart from each other, wherein the guide engages in a fixed rotational orientation relationship with the stock prosthetic implant when the two or more locating protrusions of the guide are nested with the corresponding two or more fastener apertures of the stock prosthetic implant, and wherein relative rotation between the guide and the stock prosthetic implant is configured to be prevented in said fixed rotational orientation relationship;
 an orienting feature; wherein
  the orienting feature is configured to enter a predetermined orienting relationship with a previously placed landmark while the locating protrusion extending from the lower guide surface is in mating contact with the preselected fastener aperture in the upper surface of the stock prosthetic implant to rotationally engage the guide and the stock prosthetic implant together in said fixed rotational orientation relationship.

13. The guide of claim 12, being at least one of custom manufactured and modified from a stock guide, responsive to at least one of preoperative imaging of the patient tissue and preoperative selection of the stock prosthetic implant.

14. The guide of claim 12, wherein the orienting feature includes an orienting indicator, and the orienting indicator achieves a predetermined signaling relationship with the landmark while the guide and stock prosthetic implant are in the predetermined relative guide/implant orientation.

15. The guide of claim 12, wherein the stock prosthetic implant and the guide are moved concurrently to move both the guide and stock prosthetic implant into predetermined guide and implant orientations with respect to the patient tissue.

16. The guide of claim 12, including at least one guide aperture extending through the guide body between the upper and lower guide surfaces, the guide aperture being configured to accept a landmark placed in a predetermined relationship with the patient tissue.

17. A system including a guide and a stock prosthetic implant, the guide adapted to with attachment of the stock prosthetic implant to a patient tissue, the guide comprising:
 a lower guide surface configured to contacting an upper implant surface of the stock prosthetic implant when a lower implant surface of the stock prosthetic implant is in contact with the patient tissue, at least a portion of the lower guide surface being contoured to substantially mate with at least a portion of the upper implant surface, and wherein both the lower guide surface and the upper implant surface are concave in profile;
 an upper guide surface spaced longitudinally apart from the lower guide surface by a guide body, the upper guide surface being accessible to a user when the lower guide surface is in contact with the upper implant surface;
 wherein both the upper guide surface and the lower implant surface are convex in profile;
 at least one guiding aperture extending through the guide body between the upper and lower guide surfaces at a predetermined aperture location with respect to the guide body, the at least one guiding aperture defining a predetermined target trajectory through the guide body, and the at least one guiding aperture being collinear with a corresponding one of a plurality of fastener apertures in the stock prosthetic implant when the lower guide surface is mated with the upper implant surface;
 wherein at least one of the target trajectory and the aperture location of each guiding aperture is preselected responsive to preoperative imaging of the patient tissue;
 wherein the guide includes a predetermined number of guiding apertures which is no more than a predetermined number of the plurality of fastener apertures of the stock prosthetic implant and, each guiding aperture is configured to be collinear with a predetermined one of the fastener apertures when the lower guide surface is mated with the upper implant surface, and two or more locating protrusions integrally formed with the guide body and extending from the lower guide surface toward the upper implant surface and spaced apart from each other, the two or more locating protrusions being configured to nest into preselected ones of the fastener apertures, wherein the guide is configured to be engaged together is in a fixed rotational orientation relationship with the stock prosthetic implant when the two or more locating protrusions of the guide are nested with preselected ones of the fastener apertures of the stock prosthetic implant, and wherein relative rotation between the guide and the stock prosthetic implant is configured to be prevented in said fixed rotational orientation relationship; and
 wherein the at least one locating protrusion is spaced apart from the at least one guiding aperture.

* * * * *